(12) United States Patent
Old et al.

(10) Patent No.: US 7,429,669 B2
(45) Date of Patent: Sep. 30, 2008

(54) THERAPEUTIC COMPOUNDS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/764,929

(22) Filed: Jun. 19, 2007

(65) Prior Publication Data

US 2007/0293561 A1    Dec. 20, 2007

Related U.S. Application Data

(60) Provisional application No. 60/805,285, filed on Jun. 20, 2006.

(51) Int. Cl.
*C07D 333/32* (2006.01)
*C07D 333/34* (2006.01)
*C07D 307/34* (2006.01)

(52) U.S. Cl. .............. 549/64; 549/29; 549/30; 549/429; 549/484; 548/122; 548/200; 548/215; 548/235; 548/236; 560/51; 560/53; 562/405; 562/459; 562/465; 562/464; 562/472; 564/169; 564/170

(58) Field of Classification Search ............ None
See application file for complete search history.

(56) References Cited

U.S. PATENT DOCUMENTS

| | | | |
|---|---|---|---|
| 3,980,700 | A | 9/1976 | Miyano |
| 4,073,799 | A | 2/1978 | Kondo et al. |
| 4,094,886 | A | 6/1978 | Kondo et al. |
| 4,806,668 | A * | 2/1989 | Raduechel et al. .......... 556/436 |
| 6,531,485 | B2 | 3/2003 | Cameron et al. |
| 7,323,591 | B2 * | 1/2008 | Old et al. .................. 562/472 |
| 2003/0008895 | A1 | 1/2003 | Cameron et al. |

FOREIGN PATENT DOCUMENTS

| | | |
|---|---|---|
| DE | 2359955 | 6/1975 |
| DE | 2608116 | 11/1976 |
| DE | 2708871 | 10/1977 |
| JP | 51-110557 | 9/1976 |
| JP | 4-149153 | 5/1992 |
| JP | 2001-163779 | 6/2001 |
| WO | WO97/30710 | 8/1997 |
| WO | WO2006/076370 | 7/2006 |

OTHER PUBLICATIONS

Kondo, et al., "Synthesis and Nucleophilic Ring-Opening Reactions of Activated Bicyclo-[3.1.0]Hexanes," Tetrahedron Letters (1976) No. 49, pp. 4489-4492.
Kondo, et al., "A New Steroselective Synthesis of Prostaglandins," Chem, Biochem, Pharmacol. Act. Prostanoids (1979), Pergamon; Oxford, Engl; Meeting Date 1978:185-193.
P. De Clereq, et al., "¹H-NMR Spectral Parameters of Some 1,4-Dihydroxy-2,3-Dialkylcyclopentanes . . . ," Bull. Soc. Chim. Belg. vol. 85/No. 11/1976, pp. 872-882.
P. De Clerq, et al., "Prostaglandin Synthesis Involving Catalytic Hydrogenation . . . ," Tetrahedron (1976) vol. 32, pp. 2747-2752.

* cited by examiner

*Primary Examiner*—Yvonne Eyler
*Assistant Examiner*—Yevegeny Valenrod
(74) *Attorney, Agent, or Firm*—Allergan, Inc.; Martin Voet; Brent A. Johnson

(57) ABSTRACT

Disclosed herein are compounds of the formula

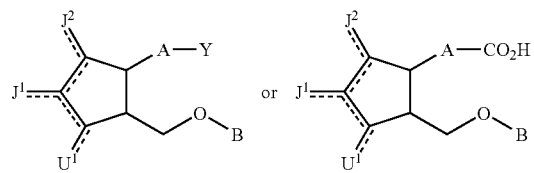

or salts or bioisosteres thereof. Therapeutic methods, medicaments, and compositions related thereto are also disclosed.

18 Claims, No Drawings

THERAPEUTIC COMPOUNDS

CROSS-REFERENCE TO RELATED APPLICATIONS

This application is based, and claims priority under 35 U.S.C. § 120 to U.S. Provisional Application Ser. No. 60/805,285, filed Jun. 20, 2006, which is hereby incorporated by reference in its entirety.

DESCRIPTION OF THE INVENTION

Disclosed herein are compounds of the formula

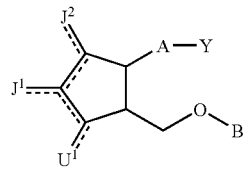

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;

$U^1$ is independently 0; S; F; Cl; Br; I; CN; or O-alkyl having 1, 2, 3, 4, 5 or 6 carbon atoms $J^1$ and $J^2$ are independently hydrogen; F; Cl; Br; I; O; OH; CN; O-alkyl having 1, 2, 3, 4, 5 or 6 carbon atoms;

alkyl having 1, 2, 3, 4, 5, or 6 carbon atoms; or $CF_3$; and

B is aryl or heteroaryl.

Also disclosed herein is a carboxylic acid or a bioisostere thereof, said carboxylic acid having a structure

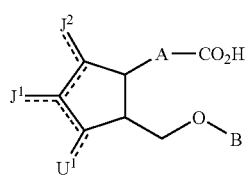

or a pharmaceutically acceptable salt thereof, or a prodrug thereof;

wherein a dashed line represents the presence or absence of a bond;

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;

$U^1$ is independently 0; S; F; Cl; Br; I; CN; or O-alkyl having 1, 2, 3, 4, 5 or 6 carbon atoms $J^1$ and $J^2$ are independently hydrogen; F; Cl; Br; I; O; OH; CN; O-alkyl having 1, 2, 3, 4, 5 or 6 carbon atoms;

alkyl having 1, 2, 3, 4, 5, or 6 carbon atoms; or $CF_3$; and

B is aryl or heteroaryl.

Any structure depicted herein, whether alone or presented with other structures, is contemplated as an individual embodiment.

Furthermore, for each individual structure presented herein, an embodiment is contemplated which comprises the compound of the structure, and/or one or more prodrugs of compounds of the structure, and/or one or more pharmaceutically acceptable salts of the compounds of the structure.

An embodiment is also contemplated which comprises the compound of the structure, and/or one or more pharmaceutically acceptable salts of the compounds of the structure.

An embodiment is also contemplated which comprises the compound of the structure, and/or one or more prodrugs of compounds of the structure.

Since a dashed line represents the presence or absence of a bond, compounds such as those according to the structures below are possible.

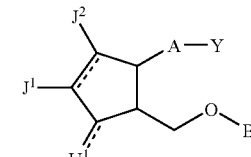

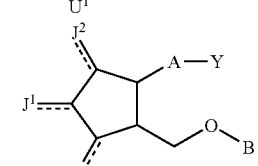

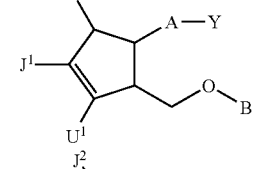

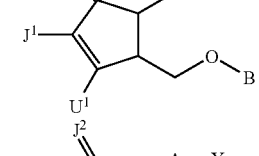

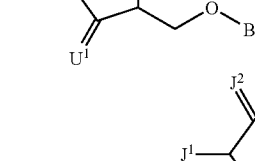

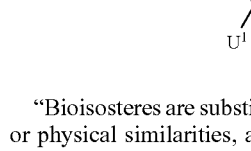

"Bioisosteres are substituents or groups that have chemical or physical similarities, and which produce broadly similar biological properties." Silverman, Richard B., *The Organic Chemistry of Drug Design and Drug Action*, 2$^{nd}$ Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated. In an ester, a hydrocarbyl moiety replaces a hydrogen atom of an acid such as in a carboxylic acid ester, e.g. CO$_2$Me, CO$_2$Et, etc.

In an amide, an amine group replaces an OH of the acid. Examples of amides include CON(R$^2$)$_2$, CON(OR$^2$)R$^2$, CON(CH$_2$CH$_2$OH)$_2$, and CONH(CH$_2$CH$_2$OH) where R$^2$ is independently H, C$_1$-C$_6$ alkyl, phenyl, or biphenyl. Moieties such as CONHSO$_2$R$^2$ are also amides of the carboxylic acid notwithstanding the fact that they may also be considered to be amides of the sulfonic acid R$^2$—SO$_3$H. The following amides are also specifically contemplated, CONSO$_2$-biphenyl, CONSO$_2$-phenyl, CONSO$_2$-heteroaryl, and CONSO$_2$-naphthyl. The biphenyl, phenyl, heteroaryl, or naphthyl may be substituted or unsubstituted.

Han et. al. (Bioorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by CO$_2$H. Thus, Y could be any group depicted below.

Carboxylic Acid Bioisosteres According to Han et al.

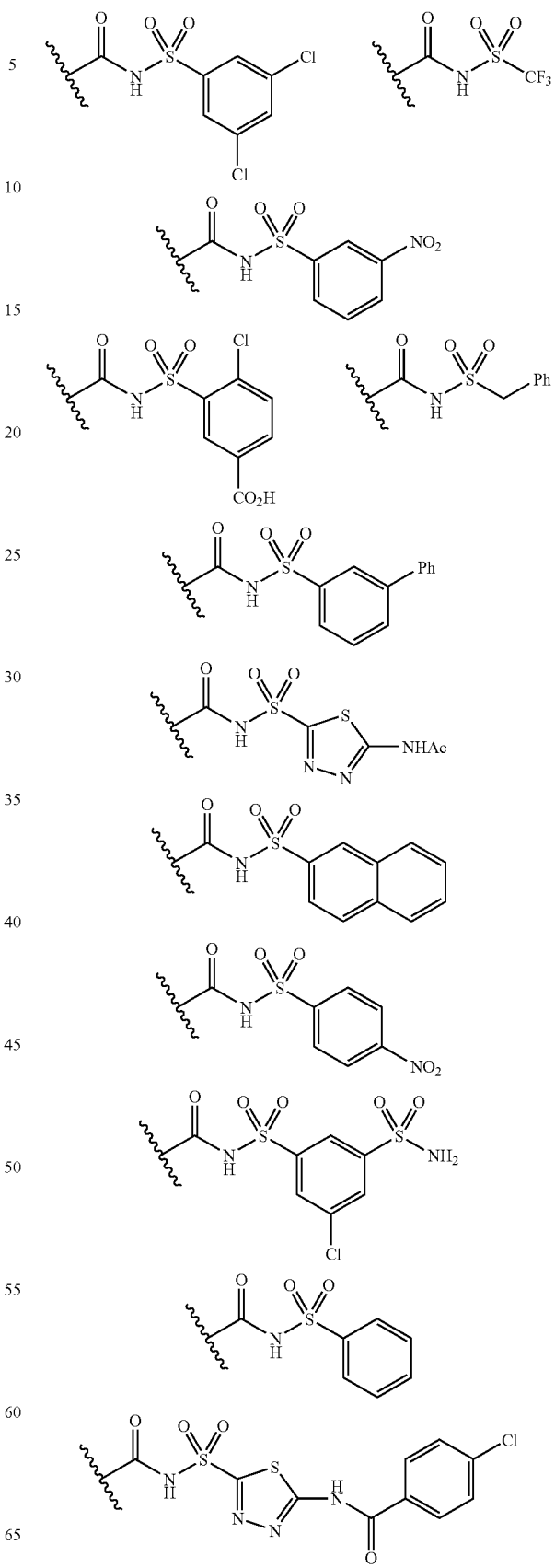

-continued

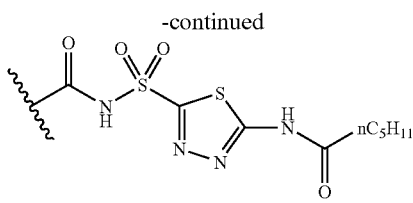

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

| Y is tetrazolyl. | | |
|---|---|---|
| Organic Acids | Esters | Amides |
| $M^1$—$CO_2H$ Carboxylic Acid | $M^1$—$CO_2R$ Carboxylic Acid Ester | $M^1$—$CO_2NR_2$ Carboxylic Acid Amide |
| $M^1$—$P(O)(OH)_2$ Phosponic Acid | $M^1$—$P(O)(OH)R$ Phosphonic Acid Ester | $M^1$—$P(O)(OH)NR_2$ Phosphonic Acid Amide |
| $M^1$—$SO_3H$ Sulfonic Acid | $M^1$—$SO_3R$ Sulfonic Acid Ester | $M^1$—$SO_3NR_2$ Sulfonic Acid Amide |
| $M^1$—$CH_2OH$ Y is hydroxymethyl | $M^1$—$CH_2OR$ Ether | |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

Additionally, if $R^2$ is $C_1$-$C_6$ alkyl, phenyl, or biphenyl, other isomeric forms of the tetrazolyl functional group such as the one shown below are also possible, unsubstituted and hydro-carbyl substituted tetrazolyl up to $C_{12}$ are considered to be within the scope of the term "tetrazolyl."

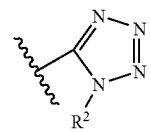

In one embodiment, Y is an organic acid functional group, or an amide or ester thereof comprising up to 14 carbon atoms; or Y is hydroxymethyl or an ether thereof comprising up to 14 carbon atoms; or Y is a tetrazolyl functional group.

In another embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

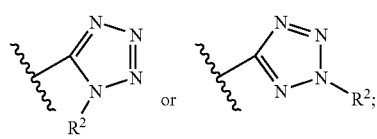

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

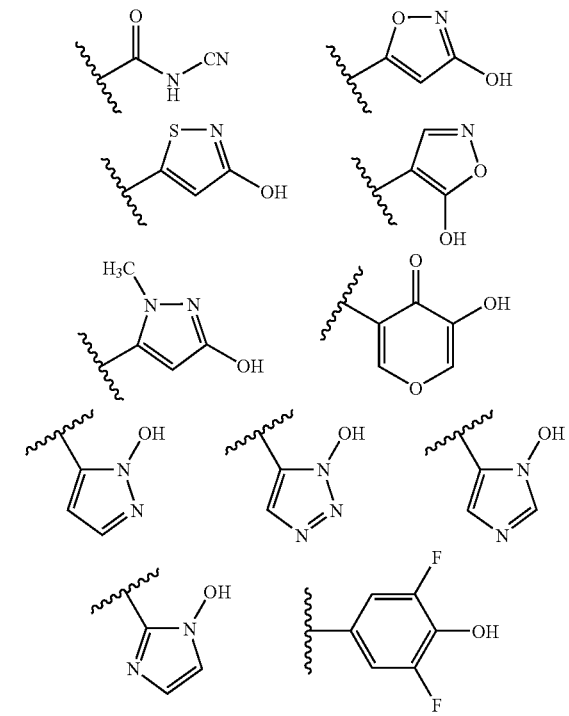

Orlek et al. (J. Med. Chem. 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem.

1996, 31, 417-425) as carboxamide replacements having improved in vivo efficacy at the benzodiazepine receptor.

Carboxylic Acid Bioisosteres According to Orlek et al.

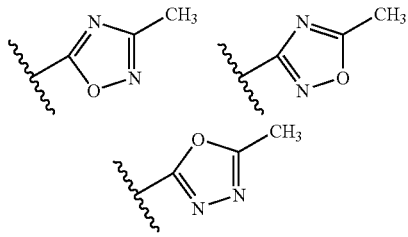

Kohara et al. (*J. Med. Chem.* 1996, 39, 5228-5235) described acidic heterocycles as suitable bioisosteres for a tetrazole. These carboxylic acid replacements were shown to be potent angiotensin 11 receptor antagonists having improved metabolic stability.

Tetrazole Bioisosteres According to Kohara et. al.

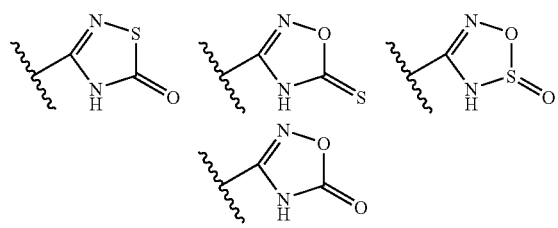

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

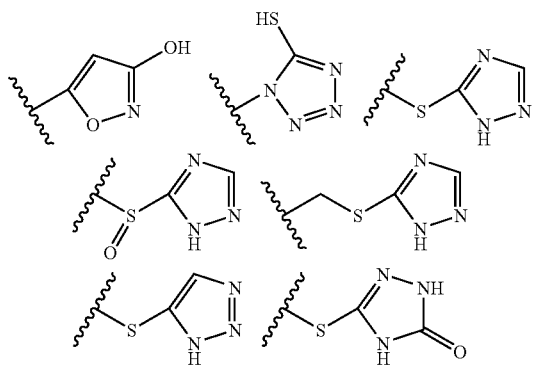

A is —$(CH_2)_6$—, cis —$CH_2CH=CH$—$(CH_2)_3$—, or —$CH_2C\equiv C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O.

While not intending to be limiting, A may be —$(CH_2)_6$—, cis —$CH_2CH=CH$—$(CH_2)_3$—, or —$CH_2C\equiv C$—$(CH_2)_3$—.

Alternatively, A may be a group which is related to one of these three moieties in that any carbon is replaced with S or O.

For example, while not intending to limit the scope of the invention in any way, A may be a moiety where S replaces one or two carbon atoms such as one of the following or the like.

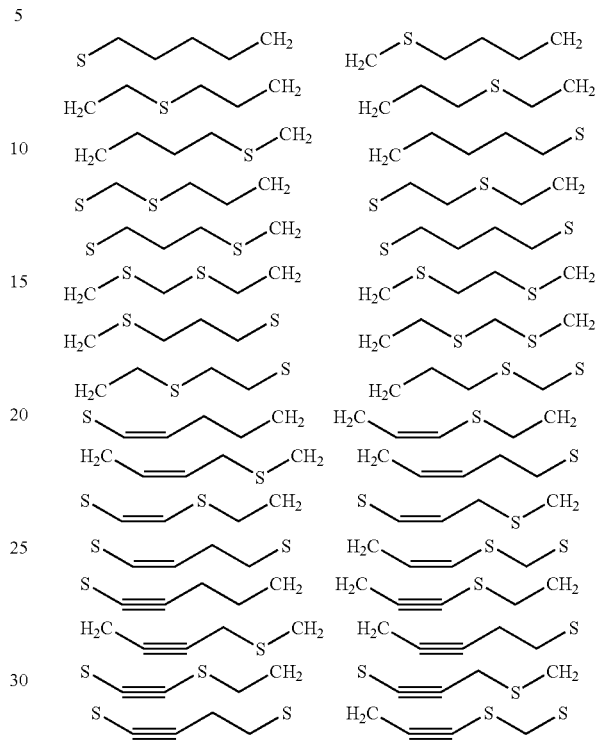

Alternatively, while not intending to limit the scope of the invention in any way, A may be a moiety where O replaces one or two carbon atoms such as one of the following or the like.

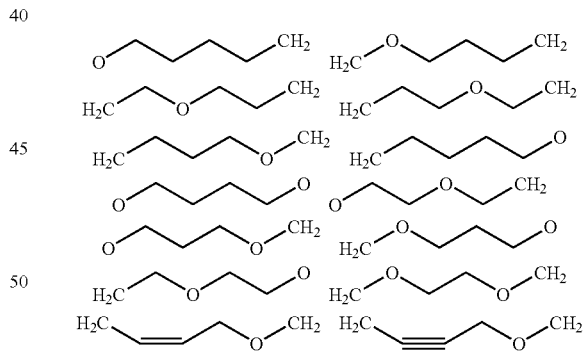

Alternatively, while not intending to limit the scope of the invention in any way, A may have an O replacing one carbon atom and an S replacing another carbon atom, such as one of the following or the like.

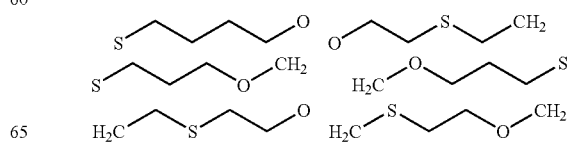

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O. In other words, while not intending to limit the scope of the invention in any way, in one embodiment A comprises 1, 2, 3, or 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like;

in another embodiment A comprises: O; 0, 1, 2, or 3 CH$_2$ moieties; and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or in another embodiment A comprises: S; 0, 1, 2, or 3 CH$_2$ moieties; and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is 2, 3, or 4 wherein one CH$_2$ may be replaced with S or O.

In another embodiment, the sum of m and o is 3 wherein one CH$_2$ may be replaced with S or O.

In another embodiment, the sum of m and o is 2 wherein one CH$_2$ may be replaced with S or O.

In another embodiment, the sum of m and o is 4 wherein one CH$_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O—Na$^+$ salt or CO$_2$H may form a CO$_2$—K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;
hydrocarbyloxy up to C$_3$;
organic acid such as CO$_2$H, SO$_3$H, P(O)(OH)$_2$, and the like, and salts thereof; CF$_3$;
halo, such as F, Cl, or Br;
hydroxyl;
NH$_2$ and alkylamine functional groups up to C$_3$;
other N or S containing substituents such as CN, NO$_2$, and the like;
and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

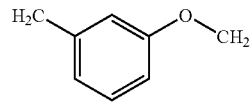

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

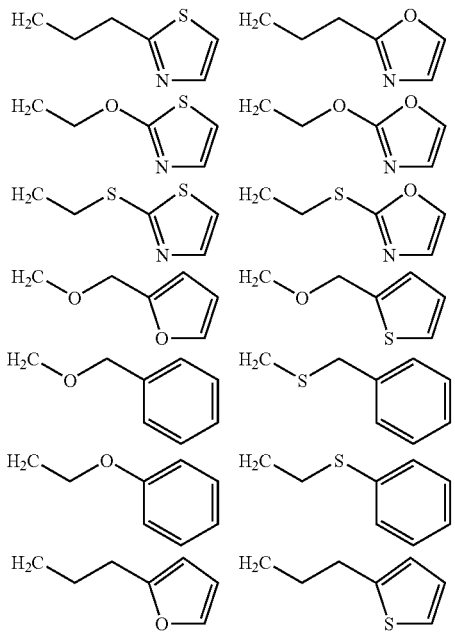

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$—O—(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)3S(CH$_2$)$_2$—.
In another embodiment A is —(CH$_2$)$_4$OCH$_2$—.
In another embodiment A is cis —CH$_2$CH=CH—CH$_2$OCH$_2$—.
In another embodiment A is —CH$_2$CH=CH—CH$_2$OCH$_2$—.

In another embodiment A is —(CH$_2$)$_2$S(CH$_2$)$_3$—.

In another embodiment A is —CH$_2$-Ph-OCH$_2$—, wherein Ph is interphenylene.

In another embodiment A is —CH$_2$-mPh-OCH$_2$—, wherein mPh is m-interphenylene.

In another embodiment A is —CH$_2$—O—(CH$_2$)$_4$—.

In another embodiment A is —CH$_2$—O—CH$_2$—Ar—, wherein Ar is 2,5-interthienylene.

In another embodiment A is —CH$_2$—O—CH$_2$—Ar—, wherein Ar is 2,5-interfurylene.

In another embodiment A is (3-methylphenoxy)methyl.

In another embodiment A is (4-but-2-ynyloxy)methyl.

In another embodiment A is 2-(2-ethylthio)thiazol-4-yl.

In another embodiment A is 2-(3-propyl)thiazol-5-yl.

In another embodiment A is 3-methoxymethyl)phenyl.

In another embodiment A is 3-(3-propylphenyl.

In another embodiment A is 3-methylphenethyl.

In another embodiment A is 4-(2-ethyl)phenyl.

In another embodiment A is 4-phenethyl.

In another embodiment A is 4-methoxybutyl.

In another embodiment A is 5-(methoxymethyl)furan-2-yl.

In another embodiment A is 5-(methoxymethyl)thiophen-2-yl.

In another embodiment A is 5-(3-propyl)furan-2-yl.

In another embodiment A is 5-(3-propyl)thiophen-2-yl.

In another embodiment A is 6-hexyl.

In another embodiment A is (Z)-6-hex-4-enyl.

In another embodiment A is —(CH$_2$)$_3$Ar—, —O(CH$_2$)$_2$Ar—, —CH$_2$OCH$_2$Ar—, —(CH$_2$)$_2$OAr, —O(CH$_2$)$_2$Ar—, —CH$_2$OCH$_2$Ar—, or —(CH$_2$)$_2$OAr, wherein Ar is monocyclic interheteroarylene.

In another embodiment Ar is interthienylene.

In another embodiment Ar is interthiazolylene.

In another embodiment Ar is interoxazolylene.

Compounds according to the each of the structures depicted below are possible.

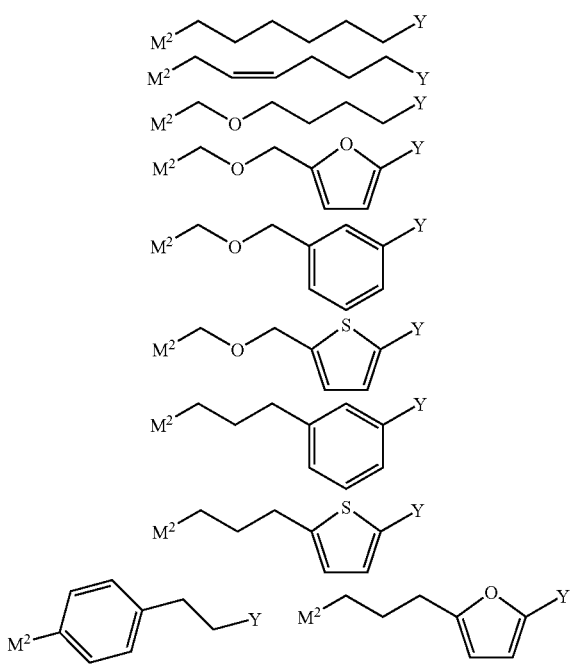

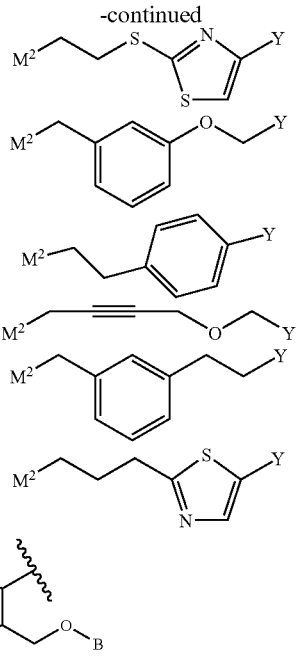

$U^1$ is independently O; S; F; Cl; Br; I; CN; or O-alkyl having 1, 2, 3, 4, 5 or 6 carbon atoms.

In one embodiment, $U^1$ is O.
In one embodiment, $U^1$ is S.
In one embodiment, $U^1$ is F.
In one embodiment, $U^1$ is Cl.
In one embodiment, $U^1$ is Br.
In one embodiment, $U^1$ is 1.
In one embodiment, $U^1$ is CN.
In one embodiment, $U^1$ is O-alkyl having 1, 2, 3, 4, 5 or 6 carbon atoms.

$J^1$ and $J^2$ are independently hydrogen; F; Cl, Br; I; O; OH; CN; O-alkyl having 1, 2, 3, 4, 5 or 6 carbon atoms; alkyl having 1, 2, 3, 4, 5, or 6 carbon atoms; or CF$_3$.

In one embodiment, $J^1$ is hydrogen.
In one embodiment, $J^1$ is F.
In one embodiment, $J^1$ is Cl.
In one embodiment, $J^1$ is Br.
In one embodiment, $J^1$ is I.
In one embodiment, $J^1$ is O.
In one embodiment, $J^1$ is OH.
In one embodiment, $J^1$ is CN.
In one embodiment, $J^1$ is O-alkyl having 1, 2, 3, 4, 5 or 6 carbon atoms.
In one embodiment, $J^1$ is alkyl having 1, 2, 3, 4, 5, or 6 carbon atoms.
In one embodiment, $J^1$ is CF$_3$.
In one embodiment, $J^2$ is hydrogen.
In one embodiment, $J^2$ is F.
In one embodiment, $J^2$ is Cl.
In one embodiment, $J^2$ is Br.
In one embodiment, $J^2$ is I.
In one embodiment, $J^2$ is O.
In one embodiment, $J^2$ is OH.
In one embodiment, $J^2$ is CN.
In one embodiment, $J^2$ is O-alkyl having 1, 2, 3, 4, 5 or 6 carbon atoms.

In one embodiment, $J^2$ is alkyl having 1, 2, 3, 4, 5, or 6 carbon atoms.

In one embodiment, $J^2$ is $CF_3$.

Thus, compounds according to the structures shown below are possible.

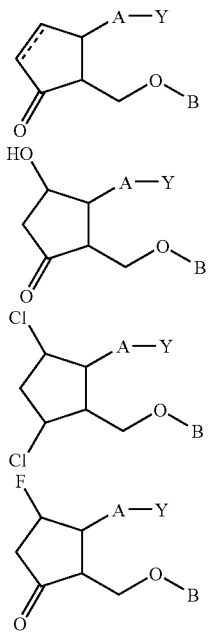 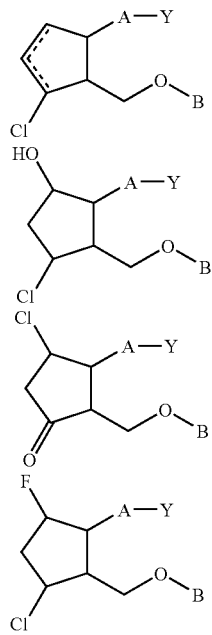

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O—$Na^+$ salt or $CO_2H$ may form a $CO_2$—$K^+$ salt. Any cation of the salt is not counted in the 20 non-hydrogen atoms. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as $OCH_3$, $OCH_2CH_3$, O-cyclohexyl, etc, up to 19 carbon atoms;

other ether substituents such as $CH_2OCH_3$, $(CH_2)_2OCH(CH_3)_2$, and the like;

thioether substituents including S-hydrocarbyl and other thioether substituents;

hydroxyhydrocarbyl, meaning hydrocarbyl-OH such as $CH_2OH$, $C(CH_3)_2OH$, etc, up to 19 carbon atoms;

nitrogen substituents such as $NO_2$, CN, and the like, including amino, such as $NH_2$, $NH(CH_2CH_3OH)$, $NHCH_3$, and the like;

carbonyl substituents, such as $CO_2H$, ester, amide, and the like;

halogen, such as chloro, fluoro, bromo, and the like fluorocarbyl, such as $CF_3$, $CF_2CF_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl and are also substituted phenyl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

Another embodiment is a compound according to the structure

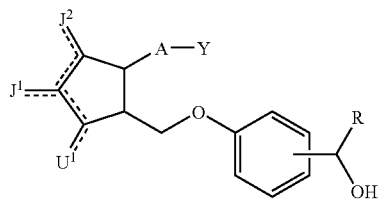

or a pharmaceutical salt thereof, or a prodrug thereof, wherein R is hydrogen or $C_{1-10}$ hydrocarbyl.

Another embodiment is a compound according to the structure

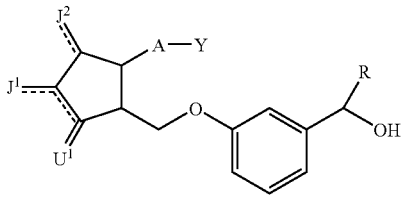

or a pharmaceutical salt thereof, or a prodrug thereof, wherein R is hydrogen or $C_{1-10}$ hydrocarbyl.

Another embodiment is a compound according to the structure

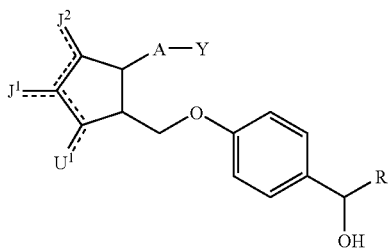

or a pharmaceutical salt thereof, or a prodrug thereof, wherein R is hydrogen or $C_{1-10}$ hydrocarbyl.

Another embodiment is a compound according to the structure

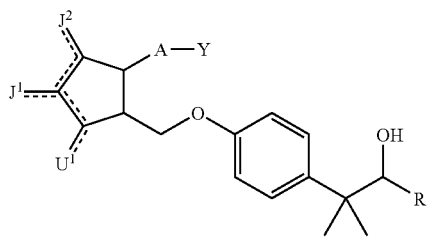

"$C_{1-10}$" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:
linear alkyl such as methyl, ethyl, propyl, n-butyl, n-pentyl, n-hexyl, and the like;
branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;
cycloalkyl such as cyclopropyl, cyclobutyl, cyclopentyl, cyclohexyl, cycloheptyl, etc.; and
alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule. Examples are —$CH_2$-Phenyl, —$CH_2$—$CH_2$-Phenyl, and the like. Arylalkyl may or may not be hydrocarbyl, depending upon whether the aryl portion has substituents with heteroatoms.

Unconjugated dienes or polyenes have one or more double bonds which are not conjugated. They may be linear, branched, or cyclic, or a combination thereof.

Combinations of the above are also possible.

In another embodiment, B is substituted or unsubstituted phenyl.

In another embodiment, B is substituted or unsubstituted thienyl.

In another embodiment, B is substituted or unsubstituted naphthyl.

In another embodiment, B is substituted or unsubstituted furyl.

In another embodiment, B is substituted or unsubstituted pyridinyl.

In another embodiment, B is substituted or unsubstituted benzothienyl.

In another embodiment, B is substituted or unsubstituted indanyl.

In another embodiment, B is substituted or unsubstituted tetralonyl.

In another embodiment, B has 1, 2, 3, 4, or 5 substituents, wherein each substituent has one or more carbon, fluorine, chlorine, bromine, oxygen, sulfur, or atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, 0, 1, 2 or 3 oxygen atoms; 0, 1, 2, or 3 sulfur atoms; 0, 1, 2, or 3 nitrogen atoms.

In another embodiment, B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, and 0, 1, 2 or 3 oxygen atoms.

In another embodiment, B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

In another embodiment, B has 1, 2, 3, or 4 alkyl substituents having 1, 2, 3, 4, 5, 6, 7, 8, 9 or 10 carbon atoms.

In another embodiment, B has a hydroxyalkyl substituent having 0, 1, 2, 3, 4, 5, 6, 7, 8, 9 or 10 carbon atoms and 1 or 2 hydroxy moieties.

In another embodiment, B has an alkyl substituent having 0, 1, 2, 3, 4, 5, 6, 7, 8, 9 or 10 carbon atoms.

In another embodiment, B has 1, 2, 3, or 4 halogen substituents.

In another embodiment, B has 1, 2, 3, or 4 chloro substituents.

In another embodiment, B has 1 chloro substituent.

In another embodiment, B has 2 chloro substituents.

In another embodiment, B has 1, 2, 3, or 4 trifluoromethyl substituents.

In another embodiment, B has 1, 2, or 3 trifluoromethyl substituents.

In another embodiment, B has 1 trifluoromethyl substituent.

In another embodiment, B has 2 trifluoromethyl substituents.

In another embodiment, B has a hydroxyl substituent.

Examples of useful moieties for B are depicted below. Each is individually contemplated as an embodiment.

| Structure: | 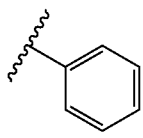 | 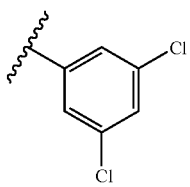 | 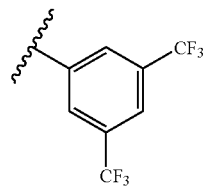 |
|---|---|---|---|
| Name: | unsubstituted phenyl | 3,5-dichlorophenyl | 3,5-di(trifluoromethyl)phenyl |
| Structure: | 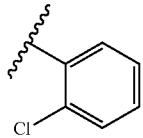 | 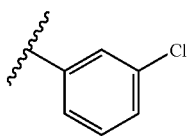 | 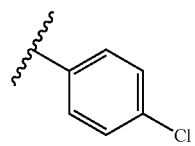 |
| Name: | 2-chlorophenyl | 3-chlorophenyl | 4-chlorophenyl |
| Structure: | 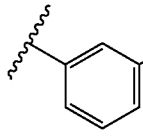 | 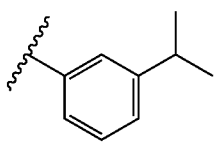 | 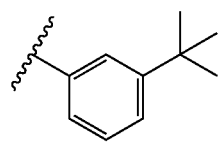 |
| Name: | 3-(trifluoromethyl)phenyl | 3-isopropylphenyl | 3-tert-butylphenyl |
| Structure: | 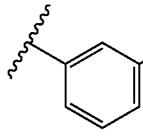 | 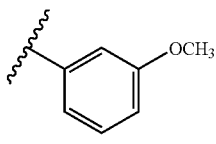 | 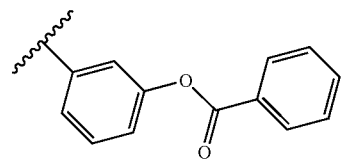 |
| Name: | 3-hydroxyphenyl | 3-methoxyphenyl | 3-(benzoyloxy)phenyl |
| Structure: | 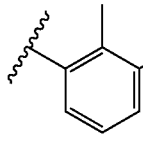 | 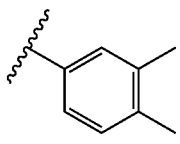 | 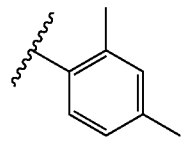 |
| Name: | 2,3-dimethylphenyl | 3,4-dimethylphenyl | 2,4-dimethylphenyl |
| Structure: | 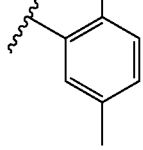 | 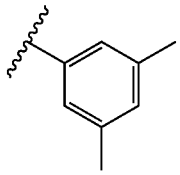 | 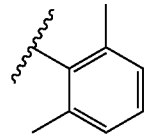 |
| Name: | 2,5-dimethylphenyl | 3,5-dimethylphenyl | 2,6-dimethylphenyl |
| Structure: | 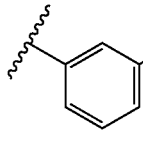 | 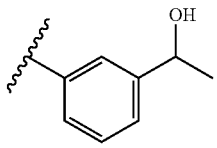 | 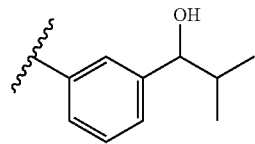 |
| Name: | 3-(hydroxymethyl)phenyl | 3-(1-hydroxyethyl)phenyl | 3-(1-hydroxy-2-methylpropyl)phenyl |

-continued

| | | |
|---|---|---|
| Structure: 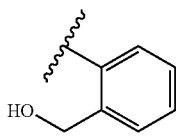 | 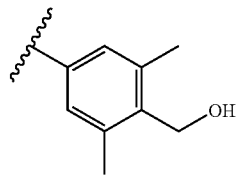 | 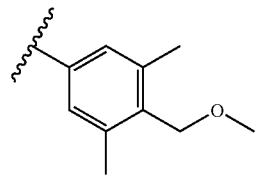 |
| Name: 2-(hydroxymethyl)phenyl | 4-(hydroxymethyl)-3,5-dimethylphenyl | 4-(methoxymethyl)-3,5-dimethylphenyl |
| Structure: 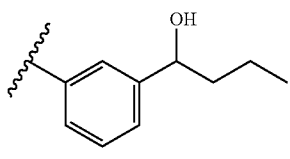 | 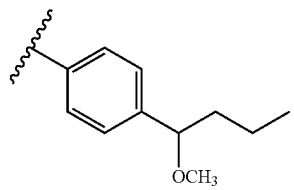 | 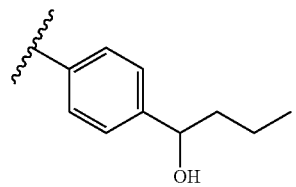 |
| Name: 3-(1-hydroxybutyl)phenyl | 4-(1-methoxybutyl)phenyl | 4-(1-hydroxybutyl)phenyl |
| Structure: 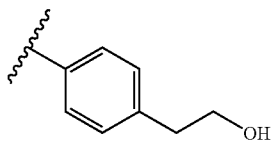 | 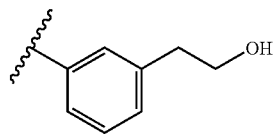 | 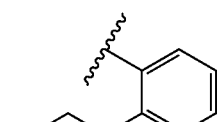 |
| Name: 4-(2-hydroxyethyl)phenyl | 3-(2-hydroxyethyl)phenyl | 2-(2-hydroxyethyl)phenyl |
| Structure: 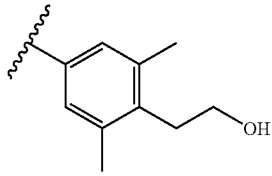 | 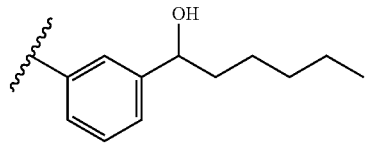 | 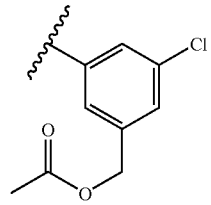 |
| Name: 4-(2-hydroxyethyl)-3,5-dimethylphenyl | 3-(1-hydroxyhexyl)phenyl | 3-(acetoxymethyl)-5-chlorophenyl |
| Structure: 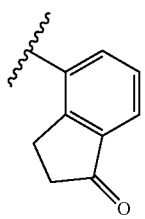 | 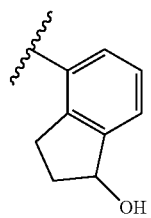 | 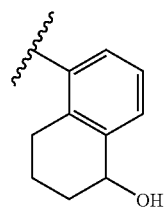 |
| Name: 1-oxo-2,3-dihydro-1H-inden-4-yl | 1-hydroxy-2,3-dihydro-1H-inden-4-yl | 5-hydroxy-5,6,7,8-tetrahydronaphthalen-1-yl |
| Structure: 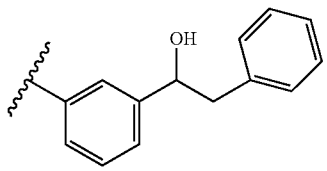 | 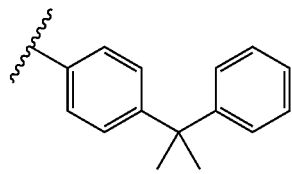 | |
| Name: 3-(1-hydroxy-2-phenylethyl)phenyl | 4-(2-phenylpropan-2-yl)phenyl | |

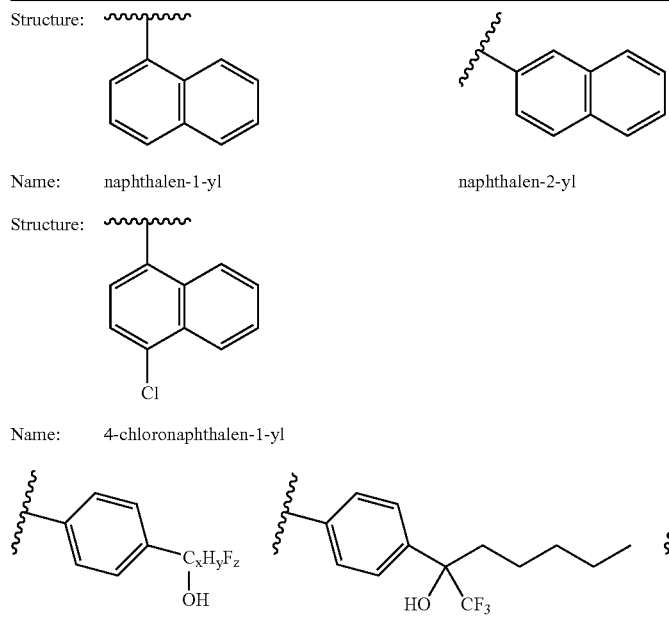

In the above embodiments, x is 5, 6, or 7, and y+z is 2x+1.

In one embodiment, x is 5 and y+z is 11.

In another embodiment, x is 6 and y+z is 13.

In another embodiment, x is 7 and y+z is 15.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

DESCRIPTION OF THE INVENTION

COMPOUND EXAMPLES

The following are hypothetical examples of useful compounds:

Compound Example 1

A compound of the formula

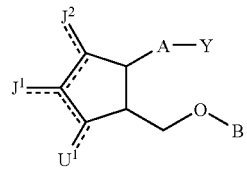

or a pharmaceutically acceptable salt thereof, or a prodrug thereof;
wherein a dashed line represents the presence or absence of a bond;
Y is an organic acid functional group, or an amide or ester thereof comprising up to 14 carbon atoms; or Y is hydroxymethyl or an ether thereof comprising up to 14 carbon atoms; or Y is a tetrazolyl functional group;
A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;
$U^1$ is independently O; S; F; Cl; Br; I; CN; or O-alkyl having 1, 2, 3, 4, 5 or 6 carbon atoms;
$J^1$ and $J^2$ are independently hydrogen; F; Cl, Br; I; O; OH; CN; O-alkyl having 1, 2, 3, 4, 5 or 6 carbon atoms; alkyl having 1, 2, 3, 4, 5, or 6 carbon atoms; or $CF_3$; and
B is aryl or heteroaryl.

Compound Example 2

A compound which is a carboxylic acid or a bioisostere thereof, said carboxylic acid having a structure

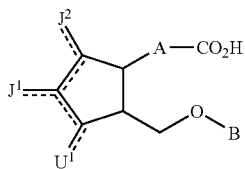

or a pharmaceutically acceptable salt thereof, or a prodrug thereof;
wherein a dashed line represents the presence or absence of a bond;
A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein one $CH_2$ may be replaced by S or O;
$U^1$ is independently O; S; F; Cl; Br; I; CN; or O-alkyl having 1, 2, 3, 4, 5 or 6 carbon atoms;
$J^1$ and $J^2$ are independently hydrogen; F; Cl, Br; I; O; OH; CN; O-alkyl having 1, 2, 3, 4, 5 or 6 carbon atoms; alkyl having 1, 2, 3, 4, 5, or 6 carbon atoms; or CF3; and
B is aryl or heteroaryl.

Compound Example 3

A compound according to compound example 1 wherein Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

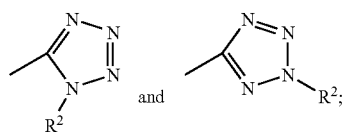

wherein $R^2$ is independently H, $C_1$-$C_6$ alkyl, unsubstituted phenyl, or unsubstituted biphenyl.

Compound Example 4

A compound according to compound example 1 or 3 of the formula

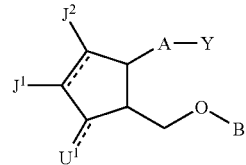

or a pharmaceutically acceptable salt thereof, or a prodrug thereof

Compound Example 5

A compound according to compound example 1 or 3 of the formula

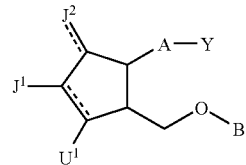

or a pharmaceutically acceptable salt thereof, or a prodrug thereof

Compound Example 6

A compound according to compound example 1 or 3 of the formula

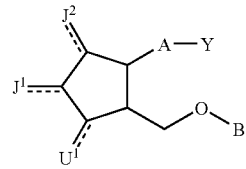

or a pharmaceutically acceptable salt thereof, or a prodrug thereof

Compound Example 7

A compound according to any one of compound examples 1 to 6 wherein A is (3-methylphenoxy)methyl.

Compound Example 8

A compound according to any one of compound examples 1 to 6 wherein A is (4-but-2-ynyloxy)methyl.

Compound Example 9

A compound according to any one of compound examples 1 to 6 wherein A is 2-(2-ethylthio)thiazol-4-yl.

Compound Example 10

A compound according to any one of compound examples 1 to 6 wherein A is 2-(3-propyl)thiazol-5-yl.

Compound Example 11

A compound according to any one of compound examples 1 to 6 wherein A is 3-(methoxymethyl)phenyl.

Compound Example 12

A compound according to any one of compound examples 1 to 6 wherein A is 3-(3-propyl)phenyl.

Compound Example 13

A compound according to any one of compound examples 1 to 6 wherein A is 3-methylphenethyl.

Compound Example 14

A compound according to any one of compound examples 1 to 6 wherein A is 4-(2-ethyl)phenyl.

Compound Example 15

A compound according to any one of compound examples 1 to 6 wherein A is 4-phenethyl.

Compound Example 16

A compound according to any one of compound examples 1 to 6 wherein A is 4-methoxybutyl.

Compound Example 17

A compound according to any one of compound examples 1 to 6 wherein A is 5-(methoxymethyl)furan-2-yl.

Compound Example 18

A compound according to any one of compound examples 1 to 6 wherein A is 5-(methoxymethyl)thiophen-2-yl.

Compound Example 19

A compound according to any one of compound examples 1 to 6 wherein A is 5-(3-propyl)furan-2-yl.

Compound Example 20

A compound according to any one of compound examples 1 to 6 wherein A is 5-(3-propyl)thiophen-2-yl.

Compound Example 21

A compound according to any one of compound examples 1 to 6 wherein A is 6-hexyl.

Compound Example 22

A compound according to any one of compound examples 1 to 6 wherein A is (Z)-6-hex-4-enyl.

Compound Example 23

A compound according to any one of compound examples 1, 3, 4 and 7 to 22 having the formula

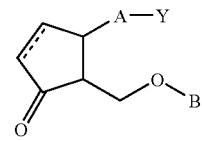

or a pharmaceutically acceptable salt thereof or a prodrug thereof.

Compound Example 24

A compound according to any one of compound examples 1, 3, and 7 to 22 having the formula

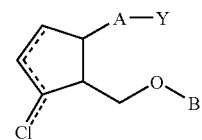

or a pharmaceutically acceptable salt thereof or a prodrug thereof.

Compound Example 25

A compound according to any one of compound examples 1, 3, and 6 to 22 having the formula

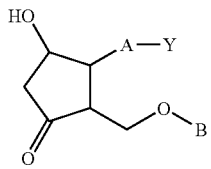

or a pharmaceutically acceptable salt thereof or a prodrug thereof.

Compound Example 26

A compound according to any one of compound examples 1, 3, and 6 to 22 having the formula

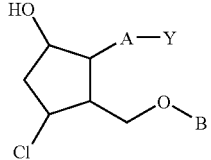

or a pharmaceutically acceptable salt thereof or a prodrug thereof.

Compound Example 27

A compound according to any one of compound examples 1, 3, and 6 to 22 having the formula

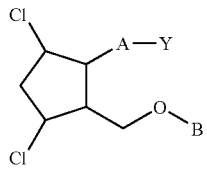

or a pharmaceutically acceptable salt thereof or a prodrug thereof.

Compound Example 28

A compound according to any one of compound examples 1, 3, and 6 to 22 having the formula

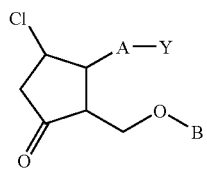

or a pharmaceutically acceptable salt thereof or a prodrug thereof.

Compound Example 29

A compound according to any one of compound examples 1, 3, and 6 to 22 having the formula

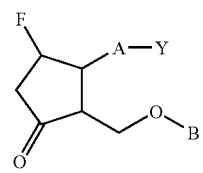

or a pharmaceutically acceptable salt thereof or a prodrug thereof.

Compound Example 30

A compound according to any one of compound examples 1, 3, and 6 to 22 having the formula

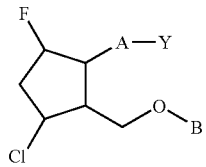

or a pharmaceutically acceptable salt thereof or a prodrug thereof.

Compound Example 31

A compound according to any one of compound examples 1 to 3, and 7 to 22, and 31 to 38 wherein $U^1$ is O.

Compound Example 32

A compound according to any one of compound examples 1 to 3, and 7 to 22, and 31 to 38 wherein $U^1$ is S.

Compound Example 33

A compound according to any one of compound examples 1 to 3, and 7 to 22, and 31 to 38 wherein $U^1$ is F.

Compound Example 34

A compound according to any one of compound examples 1 to 3, and 7 to 22, and 31 to 38 wherein $U^1$ is Cl.

Compound Example 35

A compound according to any one of compound examples 1 to 3, and 7 to 22, and 31 to 38 wherein $U^1$ is Br.

Compound Example 36

A compound according to any one of compound examples 1 to 3, and 7 to 22, and 31 to 38 wherein $U^1$ is I.

Compound Example 37

A compound according to any one of compound examples 1 to 3, and 7 to 22, and 31 to 38 wherein $U^1$ is CN.

Compound Example 38

A compound according to any one of compound examples 1 to 3, and 7 to 22, and 31 to 38 wherein $U^1$ is O-alkyl having 1, 2, 3, 4, 5 or 6 carbon atoms.

Compound Example 39

A compound according to any one of compound examples 1 to 3, and 7 to 22, and 31 to 38 wherein $J^1$ is hydrogen.

Compound Example 40

A compound according to any one of compound examples 1 to 3, and 7 to 22, and 31 to 38 wherein $J^1$ is F.

Compound Example 41

A compound according to any one of compound examples 1 to 3, and 7 to 22, and 31 to 38 wherein $J^1$ is Cl.

Compound Example 42

A compound according to any one of compound examples 1 to 3, and 7 to 22, and 31 to 38 wherein $J^1$ is Br.

Compound Example 43

A compound according to any one of compound examples 1 to 3, and 7 to 22, and 31 to 38 wherein $J^1$ is I.

Compound Example 44

A compound according to any one of compound examples 1 to 3, and 7 to 22, and 31 to 38 wherein $J^1$ is O.

Compound Example 45

A compound according to any one of compound examples 1 to 3, and 7 to 22, and 31 to 38 wherein $J^1$ is OH.

Compound Example 46

A compound according to any one of compound examples 1 to 3, and 7 to 22, and 31 to 38 wherein $J^1$ is CN.

Compound Example 47

A compound according to any one of compound examples 1 to 3, and 7 to 22, and 31 to 38 wherein $J^1$ is O-alkyl having 1, 2, 3, 4, 5 or 6 carbon atoms.

Compound Example 48

A compound according to any one of compound examples 1 to 3, and 7 to 22, and 31 to 38 wherein $J^1$ is alkyl having 1, 2, 3, 4, 5, or 6 carbon atoms.

Compound Example 49

A compound according to any one of compound examples 1 to 3, and 7 to 22, and 31 to 38 wherein $J^1$ is $CF_3$.

Compound Example 50

A compound according to any one of compound examples 1 to 3, 7 to 22, and 31 to 49 wherein $J^2$ is hydrogen.

Compound Example 51

A compound according to any one of compound examples 1 to 3, 7 to 22, and 31 to 49 wherein $J^2$ is F.

Compound Example 52

A compound according to any one of compound examples 1 to 3, 7 to 22, and 31 to 49 wherein $J^2$ is Cl.

Compound Example 53

A compound according to any one of compound examples 1 to 3, 7 to 22, and 31 to 49 wherein $J^2$ is Br.

Compound Example 54

A compound according to any one of compound examples 1 to 3, 7 to 22, and 31 to 49 wherein $J^2$ is I.

Compound Example 55

A compound according to any one of compound examples 1 to 3, 7 to 22, and 31 to 49 wherein $J^2$ is O.

Compound Example 56

A compound according to any one of compound examples 1 to 3, 7 to 22, and 31 to 49 wherein $J^2$ is OH.

Compound Example 57

A compound according to any one of compound examples 1 to 3, 7 to 22, and 31 to 49 wherein $J^2$ is CN.

Compound Example 58

A compound according to any one of compound examples 1 to 3, 7 to 22, and 31 to 49 wherein $J^2$ is O-alkyl having 1, 2, 3, 4, 5 or 6 carbon atoms.

Compound Example 59

A compound according to any one of compound examples 1 to 3, 7 to 22, and 31 to 49 wherein $J^2$ is alkyl having 1, 2, 3, 4, 5, or 6 carbon atoms.

Compound Example 60

A compound according to any one of compound examples 1 to 3, 7 to 22, and 31 to 49 wherein $J^2$ is $CF_3$.

Compound Example 61

A compound according to any one of compound examples 1 to 60 wherein B is substituted or unsubstituted phenyl.

Compound Example 62

A compound according to any one of compound examples 1 to 60 wherein B is substituted or unsubstituted thienyl.

Compound Example 63

A compound according to any one of compound examples 1 to 60 wherein B is substituted or unsubstituted naphthyl.

Compound Example 64

A compound according to any one of compound examples 1 to 60 wherein B is substituted or unsubstituted furyl.

Compound Example 65

A compound according to any one of compound examples 1 to 60 wherein B is substituted or unsubstituted pyridinyl.

Compound Example 66

A compound according to any one of compound examples 1 to 60 wherein B is substituted or unsubstituted benzothienyl.

Compound Example 67

A compound according to any one of compound examples 1 to 60 wherein B is substituted or unsubstituted indanyl.

Compound Example 68

A compound according to any one of compound examples 1 to 60 wherein B is substituted or unsubstituted tetralonyl.

Compound Example 69

A compound according to any one of compound examples 1 to 60 wherein B has 1, 2, 3, 4, or 5 substituents, wherein each substituent has one or more carbon, fluorine, chlorine, bromine, or oxygen atoms; and wherein all substituents taken together consist of 0, 1, 2, 3, 4, 5, 6, 7, 8, 9 or 10 carbon atoms; 0, 1, 2, 3, 4, 5, 6, 7, 8 or 9 fluorine atoms; 0, 1, 2 or 3 chlorine atoms, 0, 1, 2 or 3 bromine atoms, and 0, 1, 2 or 3 oxygen atoms.

Compound Example 70

A compound according to any one of compound examples 1 to 60 wherein B has a substituent of the formula $C_aH_bO_c$; wherein a is 0, 1, 2, 3, 4, 5, 6, 7, 8 or 9, b is 0, 1, 2, 3, 4, 5, 6, 7, 8, 9, 10, 11, 12, 13, 14, 15, 16, 17, 18 or 19; and c is 0, 1, 2, or 3.

Compound Example 71

A compound according to any one of compound examples 1 to 60 wherein B has 1, 2, 3, or 4 alkyl substituents having 1, 2, 3, 4, 5, 6, 7, 8, 9 or 10 carbon atoms.

Compound Example 72

A compound according to any one of compound examples 1 to 60 wherein B has a hydroxyalkyl substituent having 0, 1, 2, 3, 4, 5, 6, 7, 8, 9 or 10 carbon atoms and 1 or 2 hydroxy moieties.

Compound Example 73

A compound according to any one of compound examples 1 to 60 wherein B has an alkyl substituent having 0, 1, 2, 3, 4, 5, 6, 7, 8, 9 or 10 carbon atoms.

Compound Example 74

A compound according to any one of compound examples 1 to 60 wherein B has 1, 2, 3, or 4 halogen substituents.

Compound Example 75

A compound according to any one of compound examples 1 to 60 wherein B has 1, 2, 3, or 4 chloro subsituents.

Compound Example 76

A compound according to any one of compound examples 1 to 60 wherein B has 1 chloro substituent.

Compound Example 77

A compound according to any one of compound examples 1 to 60 wherein B has 2 chloro substituents.

Compound Example 78

A compound according to any one of compound examples 1 to 60 wherein B has 1, 2, 3, or 4 trifluoromethyl substituents.

Compound Example 79

A compound according to any one of compound examples 1 to 60 wherein B has 1, 2, or 3 trifluoromethyl substituents.

Compound Example 80

A compound according to any one of compound examples 1 to 60 wherein B has 1 trifluoromethyl substituent.

Compound Example 81

A compound according to any one of compound examples 1 to 60 wherein B has 2 trifluoromethyl substituents.

Compound Example 82

A compound according to any one of compound examples 1 to 60 wherein B has a hydroxyl substituent.

Compound Example 83

A compound according to any one of compound examples 1 to 61 wherein B is unsubstituted phenyl.

Compound Example 84

A compound according to any one of compound examples 1 to 61 wherein B is 3,5-dichlorophenyl.

Compound Example 85

A compound according to any one of compound examples 1 to 61 wherein B is 3,5-di(trifluoromethyl)phenyl.

Compound Example 86

A compound according to any one of compound examples 1 to 61 wherein B is 2-chlorophenyl.

Compound Example 87

A compound according to any one of compound examples 1 to 61 wherein B is 3-chlorophenyl.

Compound Example 88

A compound according to any one of compound examples 1 to 61 wherein B is 4-chlorophenyl.

Compound Example 89

A compound according to any one of compound examples 1 to 61 wherein B is 3-(trifluoromethyl)phenyl.

Compound Example 90

A compound according to any one of compound examples 1 to 61 wherein B is 3-isopropylphenyl.

Compound Example 91

A compound according to any one of compound examples 1 to 61 wherein B is 3-tert-butylphenyl.

Compound Example 92

A compound according to any one of compound examples 1 to 61 wherein B is 3-hydroxyphenyl.

Compound Example 93

A compound according to any one of compound examples 1 to 61 wherein B is 3-methoxyphenyl.

Compound Example 94

A compound according to any one of compound examples 1 to 61 wherein B is 3-(benzoyloxy)phenyl.

Compound Example 95

A compound according to any one of compound examples 1 to 61 wherein B is 2,3-dimethylphenyl.

Compound Example 96

A compound according to any one of compound examples 1 to 61 wherein B is 3,4-dimethylphenyl.

Compound Example 97

A compound according to any one of compound examples 1 to 61 wherein B is 2,4-dimethylphenyl.

Compound Example 98

A compound according to any one of compound examples 1 to 61 wherein B is 2,5-dimethylphenyl.

Compound Example 99

A compound according to any one of compound examples 1 to 61 wherein B is 3,5-dimethylphenyl.

Compound Example 100

A compound according to any one of compound examples 1 to 61 wherein B is 2,6-dimethylphenyl.

Compound Example 101

A compound according to any one of compound examples 1 to 61 wherein B is 3-(hydroxymethyl)phenyl.

Compound Example 102

A compound according to any one of compound examples 1 to 61 wherein B is 3-(1-hydroxyethyl)phenyl.

Compound Example 103

A compound according to any one of compound examples 1 to 61 wherein B is 3-(1-hydroxy-2-methylpropyl)phenyl.

Compound Example 104

A compound according to any one of compound examples 1 to 61 wherein B is 2-(hydroxymethyl)phenyl.

Compound Example 105

A compound according to any one of compound examples 1 to 61 wherein B is 4-(hydroxymethyl)-3,5-dimethylphenyl.

Compound Example 106

A compound according to any one of compound examples 1 to 61 wherein B is 4-(methoxymethyl)-3,5-dimethylphenyl.

Compound Example 107

A compound according to any one of compound examples 1 to 61 wherein B is 3-(1-hydroxybutyl)phenyl.

Compound Example 108

A compound according to any one of compound examples 1 to 61 wherein B is 4-(1-methoxybutyl)phenyl.

Compound Example 109

A compound according to any one of compound examples 1 to 61 wherein B is 4-(1-hydroxybutyl)phenyl.

Compound Example 110

A compound according to any one of compound examples 1 to 61 wherein B is 4-(2-hydroxyethyl)phenyl.

Compound Example 111

A compound according to any one of compound examples 1 to 61 wherein B is 3-(2-hydroxyethyl)phenyl.

Compound Example 112

A compound according to any one of compound examples 1 to 61 wherein B is 2-(2-hydroxyethyl)phenyl.

Compound Example 113

A compound according to any one of compound examples 1 to 61 wherein B is 4-(2-hydroxyethyl)-3,5-dimethylphenyl.

Compound Example 114

A compound according to any one of compound examples 1 to 61 wherein B is 3-(1-hydroxyhexyl)phenyl.

Compound Example 115

A compound according to any one of compound examples 1 to 61 wherein B is 3-(acetoxymethyl)-5-chlorophenyl.

Compound Example 116

A compound according to any one of compound examples 1 to 61 wherein B is 1-oxo-2,3-dihydro-1H-inden-4-yl.

Compound Example 117

A compound according to any one of compound examples 1 to 61 wherein B is 1-hydroxy-2,3-dihydro-1H-inden-4-yl.

Compound Example 118

A compound according to any one of compound examples 1 to 61 wherein B is 5-hydroxy-5,6,7,8-tetrahydronaphthalen-1-yl.

Compound Example 119

A compound according to any one of compound examples 1 to 61 wherein B is 3-(1-hydroxy-2-phenylethyl)phenyl.

Compound Example 120

A compound according to any one of compound examples 1 to 61 wherein B is 4-(2-phenylpropan-2-yl)phenyl.

Compound Example 121

A compound according to any one of compound examples 1 to 60 wherein B is naphthalen-2-yl.

Compound Example 122

A compound according to any one of compound examples 1 to 60 wherein B is naphthalen-1-yl.

Compound Example 123

A compound according to any one of compound examples 1 to 60 wherein B is 4-chloronaphthalen-1-yl.

The following are hypothetical examples of compositions, kits, methods, uses, and medicaments employing the hypothetical compound examples.

Composition Example

A composition comprising a compound according to any one of compound examples 1 to 123, wherein said composition is a liquid which is ophthalmically acceptable.

Medicament Examples

Use of a compound according to any one of compound examples 1 to 123 in the manufacture of a medicament for the treatment of glaucoma or ocular hypertension in a mammal.

Use of a compound according to any one of compound examples 1 to 123 in the manufacture of a medicament for the treatment of baldness in a person.

A medicament comprising a compound according to any one of compound examples 1 to 123, wherein said composition is a liquid which is ophthalmically acceptable.

Method Example

A method comprising administering a compound according to any one of compound examples 1 to 123 to a mammal for the treatment of glaucoma or ocular hypertension.

Kit Example

A kit comprising a composition comprising compound according to any one of compound examples 1 to 123, a container, and instructions for administration of said composition to a mammal for the treatment of glaucoma or ocular hypertension.

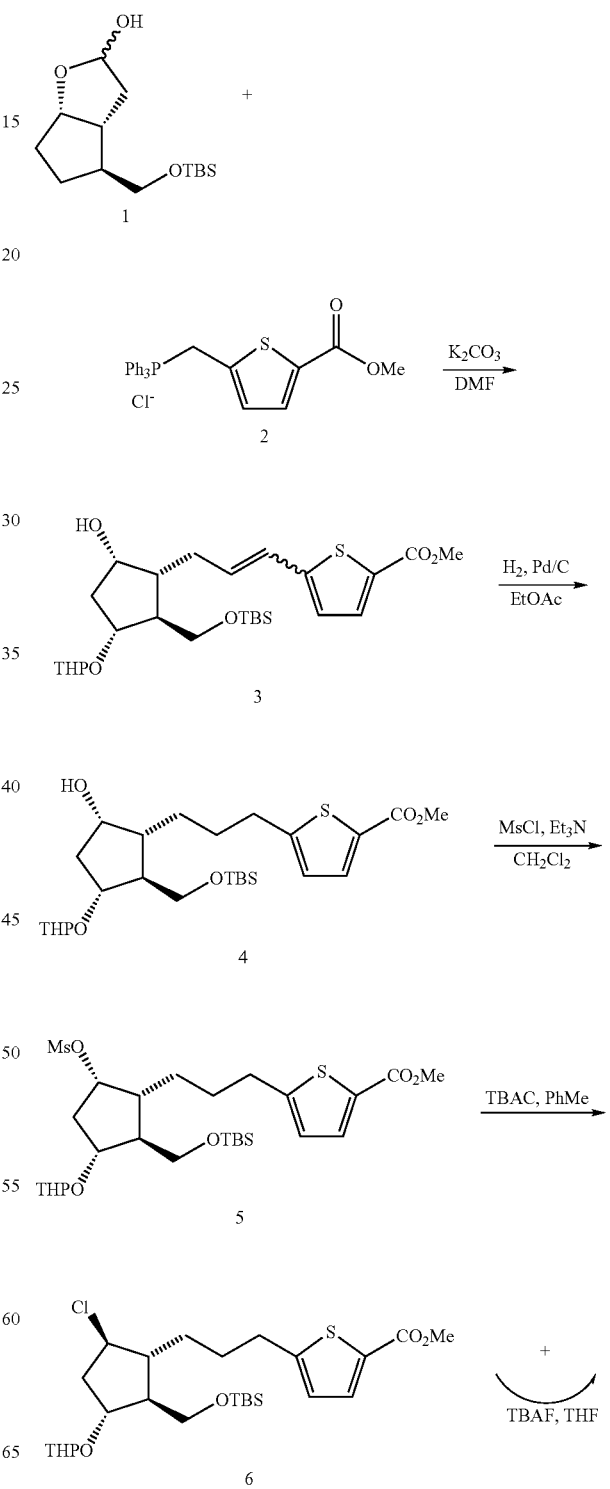

Synthetic Methods

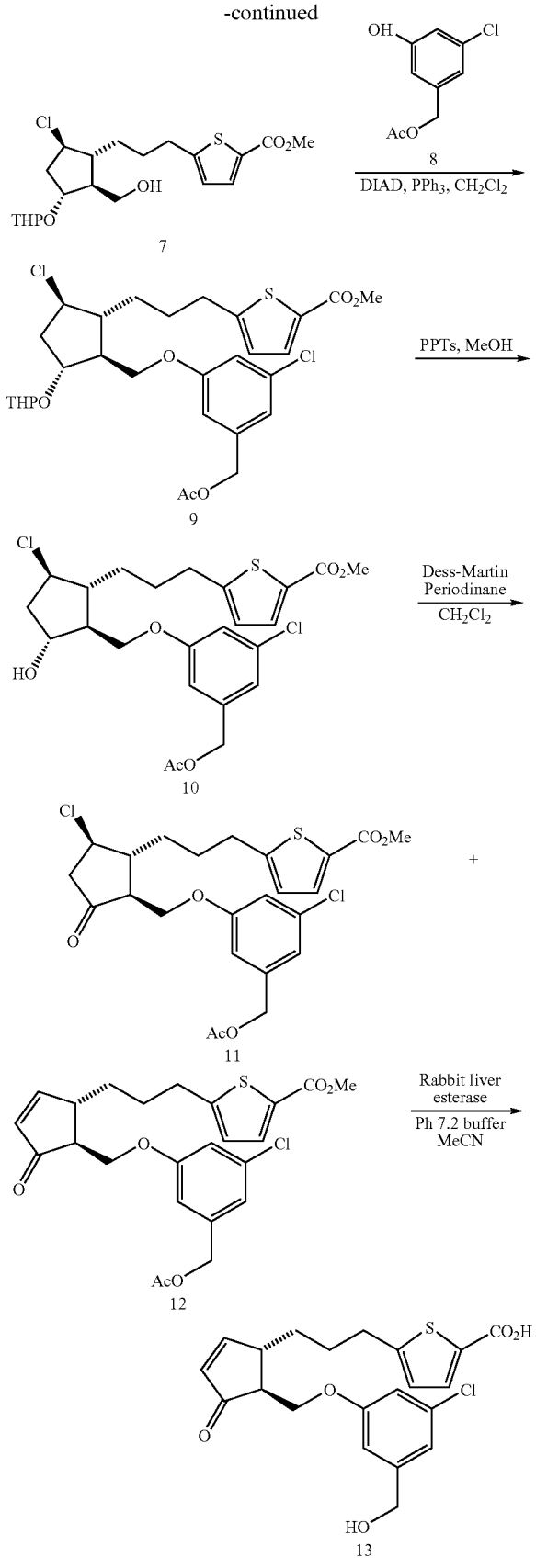

Synthetic Example 1

5-{3-[(1S,5S)-5-(3-Chloro-5-hydroxymethyl-phenoxymethyl)-4-oxo-cyclopent-2-enyl]-propyl}-thiophene-2-carboxylic acid (13)

Step 1. Wittig Reaction of Lactol 1 and Phosphonate 2 to Afford Alkene 3

Potassium carbonate (99.99%, 2.25 g, 16.3 mmol) was added to phosphonate 2 (see *Collect. Czech. Chem. Commun.* 1994, 58,138-148, 2.90 g, 6.40 mmol) in DMF (11 mL) at 0° C. After 30 min at 0° C., a solution of known lactol 1 (1.20 g, 3.22 mmol) in DMF (11 mL+10 mL) was added. The reaction mixture was allowed to rt and stirred overnight. The reaction mixture was then poured into water and extracted with EtOAc (3×). The combined extracts were washed with brine then dried (MgSO$_4$), filtered and concentrated in vacuo. Purification of the crude residue by flash column chromatography on silica gel (hexane→30% EtOAc/hexane, gradient) afforded 1.50 g (91%) of alkene 3.

Step 2. Hydrogenation of Alkene 3 to Give 4

Palladium on carbon (10 wt. %, 321 mg) was added to a solution of alkene 3 (1.50 g, 2.94 mmol) in EtOAc (59 mL). A hydrogen atmosphere was established by evacuating and refilling with hydrogen (5×) and the reaction mixture was stirred under a balloon of hydrogen for 6 h. The reaction mixture was filtered through celite, washing with EtOAc, and the filtrate was concentrated in vacuo to afford 1.51 g (quant.) of saturated compound 4.

Step 3. Mesylation of 4 to Give 5

Triethylamine (316 μL, 2.27 mmol) and methanesulfonyl chloride (142 μL, 1.80 mmol) were added sequentially to a solution of 4 (769 mg, 1.50 mmol) in CH$_2$Cl$_2$ (11.3 mL) at 0° C. The reaction mixture was allowed to warm to rt and stirred at rt overnight. Saturated aqueous NaHCO$_3$ (20 mL) was added, CH$_2$Cl$_2$ was removed in vacuo, and the remaining mixture was extracted with EtOAc (3×20 mL). The combined organic extracts were dried (MgSO$_4$), filtered and concentrated in vacuo to afford 880 mg (99%) of the desired mesylate 5, which was used without further purification.

Step 4. Conversion of Mesylate 5 to Chloride 6 and Alcohol 7

Tetrabutylammonium chloride (2.0 g, 7.2 mmol) was added to a solution of 5 (880 mg, 1.5 mmol) in toluene (15 mL). The reaction mixture was heated at 40° C. for 18 h. The cooled mixture was diluted with brine (30 mL) and extracted with EtOAc (3×50 mL). The combined organic extracts were dried (MgSO$_4$), filtered and concentrated in vacuo. Purification of the crude residue by flash column chromatography on silica gel (hexane→EtOAc, gradient) afforded 230 mg (29%) of chloride 6 and 170 mg (27%) of alcohol 7.

Step 5. Desilylation of 6 to Give Alcohol 7

Tetrabutylammonium fluoride (0.345 mL of a 1.0 M THF solution, 0.345 mmol) was added to a solution of 6 (61 mg, 0.11 mmol) in THF (5.4 mL) at rt. After 18 h at rt, the reaction mixture was partitioned between EtOAc (15 mL) and H$_2$O (10 mL). The phases were separated and the aqueous phase was extracted with EtOAc (2×10 mL). The combined organic phase washed with brine (50 mL) then dried (MgSO$_4$), filtered and concentrated in vacuo. Purification of the crude residue by flash column chromatography on silica gel (hexane→EtOAc, gradient) afforded 10 mg (21%) of alcohol 7.

Step 6. Mitsunobu Reaction of 7 and Phenol 8 to Give 9

Triphenylphosphine (160 mg, 0.61 mmol) and diisopropyl azodicarboxylate (DIAD, 90 μL, 0.49 mmol) were added to a solution of alcohol 7 (170 mg, 0.41 mmol) and phenol 8 (see U.S. Provisional Application No. 60/757,696, filed on Jan. 10, 2006, incorporated by reference herein, 81 mg, 0.40 mmol) in $CH_2Cl_2$ (2.0 mL). After stirring 18 h at rt, the mixture was partitioned between $CH_2Cl_2$ (15 mL) and saturated aqueous $NaHCO_3$ (20 mL). The phases were separated and the aqueous phase was extracted with $CH_2Cl_2$ (2×20 mL). The combined organic phase washed with brine (15 mL) then the organic phase was dried ($MgSO_4$) filtered and concentrated in vacuo. Purification of the residue by flash column chromatography on silica gel (hexane→EtOAc, gradient) afforded 170 mg (70%) of 9.

Step 7. Deprotection of 9 to Give 10

Pyridinium p-toluenesulfonate (PPTs, 7 mg, 0.028 mmol) was added to a solution of 9 (170 mg, 0.28 mmol) in methanol (2.8 mL) at rt. The solution was heated at 40° C. overnight, then cooled and concentrated in vacuo. Purification of the crude residue by flash column chromatography on silica gel (hexane→EtOAc, gradient) afforded 90 mg (62%) of 10.

Step 8. Oxidation of 10 to Give 11 and 12

Dess-Martin periodinane (35 mg, 0.083 mmol) was added to a solution of 10 (35 mg, 0.068 mmol) in $CH_2Cl_2$ (3.0 mL) at 0° C. and the mixture was allowed to warm to rt. After 2 h at rt, the mixture was partitioned between $CH_2Cl_2$ (5 mL) and $H_2O$ (5 mL). The phases were separated and the aqueous phase was extracted with $CH_2Cl_2$ (2×5 mL). The combined organic phase washed with brine (5 mL) then the organic phase was dried ($MgSO_4$) filtered and concentrated in vacuo. Purification of the residue by flash column chromatography on silica gel (hexane→EtOAc, gradient) afforded 30 mg (~87%) of a mixture of 11 and 12 (approximately 4:1 in favor of 11).

Step 9. Deprotection of 11/12 to Give 13.

Rabbit liver esterase (134 units/mg, 6 mg) was added to a mixture of 11 and 12 from step 8 above (15 mg, 0.03 mmol) and pH 7.2 buffer (2.4 mL). After 10 min at rt, MeCN (0.16 mL) was added. After stirring at rt for 24 h, the reaction mixture was concentrated to dryness. Purification of the resulting crude residue by flash column chromatography on silica gel (10% $MeOH/CH_2Cl_2$) afforded 5 mg (~40%) of title compound 13.

Synthetic Example 2

5-{3-[(1S,2S)-2-(3-Chloro-5-hydroxymethyl-phenoxymethyl)-3-oxo-cyclopentyl]-propyl}-thiophene-2-carboxylic acid (15)

Step 1. Deprotection of 11/12 to Give 12/13.

Rabbit liver esterase (134 units/mg, 6 mg) was added to a mixture of 11 and 12 from Example 1, step 8 above (15 mg, ~0.03 mmol) and pH 7.2 buffer (2.4 mL). After 10 min at rt, MeCN (0.16 mL) was added. After stirring at rt for 24 h, the reaction mixture was concentrated to dryness to afford 10 mg (~73%) of a mixture of 12 and 13 (approximately 3:1 in favor of 12), which was taken on without further purification.

Step 2. Hydrogenation of 12/13 to Give 14/15

Palladium on carbon (10 wt. %, 1 mg) was added to a mixture of 12 and 13 (10 mg, ~0.022 mmol) in EtOAc (0.42 mL). A hydrogen atmosphere was established by evacuating and refilling with hydrogen (10×) and the reaction mixture was stirred under a balloon of hydrogen for 6 h. The reaction mixture was filtered through celite, washing with EtOAc, and the filtrate was concentrated in vacuo. Purification of the resulting crude residue by flash column chromatography on silica gel (10% $MeOH/CH_2Cl_2$) afforded 7 mg (~68%) of ester 14 and 2.7 mg (30%) of title compound 15.

It is envisioned that intermediates such as 12 may react with nucleophiles such as alkyl copper reagents to afford compounds that have alkyl groups at C-9. It is further envisioned that intermediates such as 14 may be reacted with lithium diisopropylamide (LDA, or some other suitable base) followed by an electrophile such as an alkyl halide or dimethyl dioxirane to afford compounds that have an alkyl group or a hydroxyl group at C-10. It is also envisioned that intermediates such as 12 may react with appropriate reagents such that an epoxide or diol at C-9-C-10 may result. Furthermore, intermediates such as 12 and 14 may serve as precursor to compounds in which the ketone has been replaced by a chloro, fluoro, or cyano group. In these cases, the ketone is first reduced to the corresponding alcohol, which is then converted into the corresponding mesylate, which then is converted into the desired halo or cyano moiety. The intermediate alcohol and its corresponding ether and ester derivatives are also desired.

Biology Examples

Binding Data

Ki

Competition binding experiments were performed in a medium containing Hank's balanced salt solution, Hepes 20 mM, pH 7.3, membranes (~60 μg protein) or 2×10$^5$ cells from HEK 293 cells stably expressing human EP2 receptors, [$^3$H]

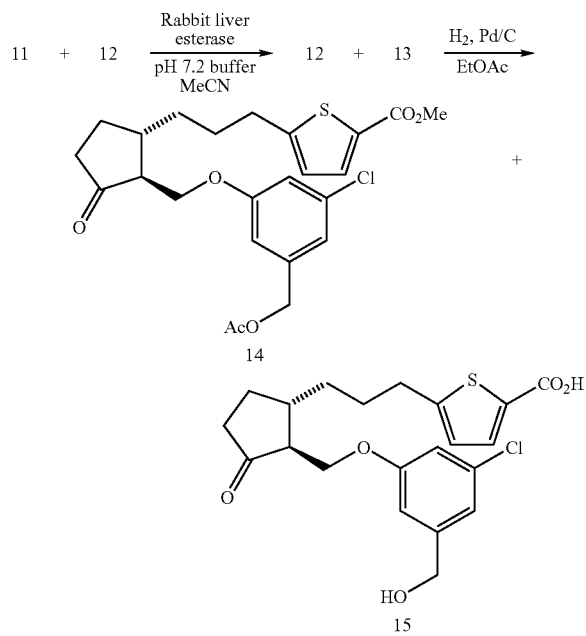

PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\square}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_2$, was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3,4}$/Gqi5; $hEP_4$/Gqs5); $PGF_2$, (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an n>3.

cAMP Assay

A 384-well drug plate was prepared to contain 6 test compounds, PGE2 and cAMP in 16 serial dilutions in triplicate, using a Biomek station. HEK-EBNA cells expressing a target PG receptor subtype (EP2 or EP4) were suspended in a stimulation buffer (HBSS, 0.1% BSA, 0.5 mM IBMX and 5 mM HEPES, pH 7.4) in a density of $10^4$ cells/5 μl. The reaction was initiated by mixing 5 μL drug dilutions with 5 μl of HEK-EBNA cells in a well, carried out for 30 min at room temperature, and followed by the addition of 5 μl anti-cAMP acceptor beads in the control buffer with Tween-20 (25 mM NaCl, 0.03% Tween-20, 5 mM HEPES, pH7.4). After 30 min in the dark at room temperature, the mixtures were incubated with 15 μl biotinylated-cAMP/strepavidin donor beads in Lysis/Detection buffer (0.1% BSA, 0.3% Tween-20 and 5 mM HEPES, pH7.4) for 45 min at the room temperature. Fluorescence changes were read using a Fusion-alpha HT microplate reader.

The results of the binding and activity studies, presented in Table 1 below, demonstrate that the compounds disclosed herein are selective prostaglandin $EP_2$ agonists, and are thus useful for the treatment of glaucoma, ocular hypertension, and other diseases or conditions.

TABLE 1

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | Ki | hFP | hEP1 | hEP3A | hTP | hIP | hDP |
| 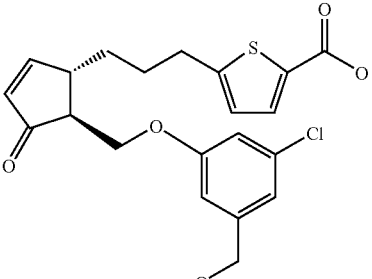 | NT | 8.7 | 201 | NA | NT | NA | NA | NA | NA | NA | NA |
| 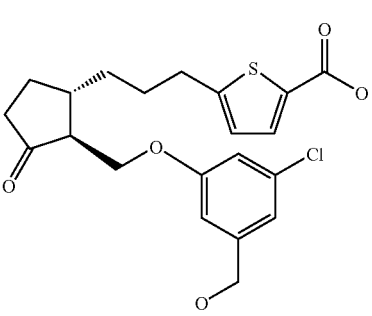 | NT | 457 | 300 | NA | >10000 | NT | NT | NT | NT | NT | NT |

Treatment Examples

The following are hypothetical examples demonstrating how a person may be treated with the compounds disclosed herein.

Treatment Example 1

An aqueous liquid containing 0.1% of H1 is given topically to the eye of a person suffering from elevated intraocular pressure. A few hours after administration, the person's intraocular pressure is reduced. The drop is administered twice a day, and pressure remains low for as long as the treatment is continued.

Treatment Example 2

An aqueous liquid containing 0.1% of H2 is given topically to the eye of a person suffering from elevated intraocular pressure. A few hours after administration, the person's intraocular pressure is reduced. The drop is administered twice a day, and pressure remains low for as long as the treatment is continued.

Treatment Example 3

An aqueous liquid containing 0.1% of H3 is given topically to the eye of a person suffering from elevated intraocular pressure. A few hours after administration, the person's intraocular pressure is reduced. The drop is administered twice a day, and pressure remains low for as long as the treatment is continued.

Treatment Example 4

An aqueous liquid containing 0.1% of H4 is given topically to the eye of a person suffering from elevated intraocular pressure. A few hours after administration, the person's intraocular pressure is reduced. The drop is administered twice a day, and pressure remains low for as long as the treatment is continued.

Treatment Example 5

An aqueous liquid containing 0.1% of H5 is given topically to the eye of a person suffering from elevated intraocular pressure. A few hours after administration, the person's intraocular pressure is reduced. The drop is administered twice a day, and pressure remains low for as long as the treatment is continued.

Treatment Example 6

An aqueous liquid containing 0.1% of H6 is given topically to the eye of a person suffering from elevated intraocular pressure. A few hours after administration, the person's intraocular pressure is reduced. The drop is administered twice a day, and pressure remains low for as long as the treatment is continued.

Treatment Example 7

An aqueous liquid containing 0.1% of H7 is given topically to the eye of a person suffering from elevated intraocular pressure. A few hours after administration, the person's intraocular pressure is reduced. The drop is administered twice a day, and pressure remains low for as long as the treatment is continued.

Treatment Example 8

An aqueous liquid containing 0.1% of H8 is given topically to the eye of a person suffering from elevated intraocular pressure. A few hours after administration, the person's intraocular pressure is reduced. The drop is administered twice a day, and pressure remains low for as long as the treatment is continued.

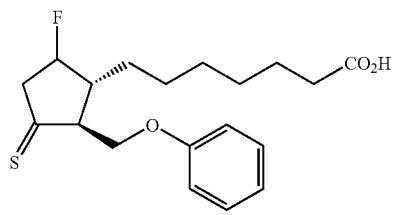
H1

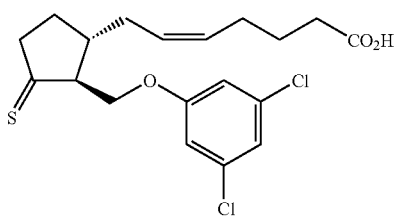
H2

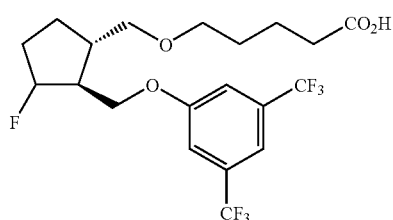
H3

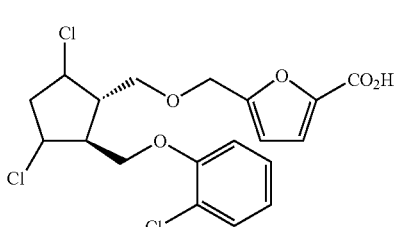
H4

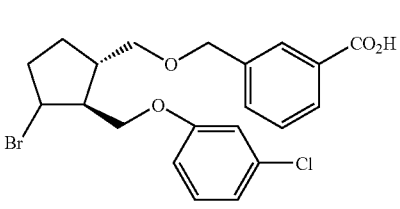
H5

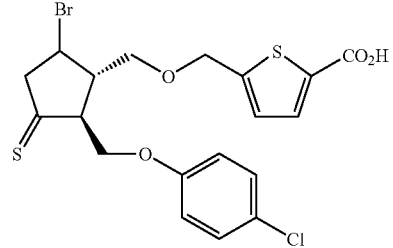
H6

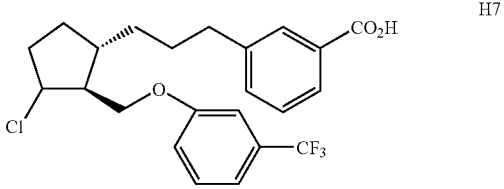
H7

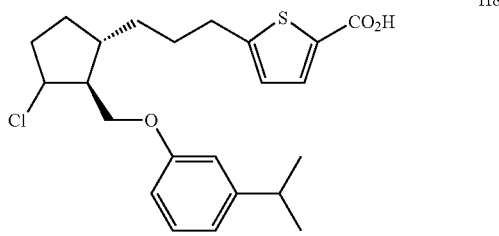
H8

Treatment Example 9

An aqueous liquid containing 0.1% of H9 is given topically to the eye of a person suffering from elevated intraocular pressure. A few hours after administration, the person's intraocular pressure is reduced. The drop is administered twice a day, and pressure remains low for as long as the treatment is continued.

Treatment Example 10

An aqueous liquid containing 0.1% of H10 is given topically to the eye of a person suffering from elevated intraocular pressure. A few hours after administration, the person's intraocular pressure is reduced. The drop is administered twice a day, and pressure remains low for as long as the treatment is continued.

Treatment Example 11

An aqueous liquid containing 0.1% of H11 is given topically to the eye of a person suffering from elevated intraocular pressure. A few hours after administration, the person's intraocular pressure is reduced. The drop is administered twice a day, and pressure remains low for as long as the treatment is continued.

Treatment Example 12

An aqueous liquid containing 0.1% of H12 is given topically to the eye of a person suffering from elevated intraocular pressure. A few hours after administration, the person's intraocular pressure is reduced. The drop is administered twice a day, and pressure remains low for as long as the treatment is continued.

Treatment Example 13

An aqueous liquid containing 0.1% of H13 is given topically to the eye of a person suffering from elevated intraocular pressure. A few hours after administration, the person's intraocular pressure is reduced. The drop is administered twice a day, and pressure remains low for as long as the treatment is continued.

Treatment Example 14

An aqueous liquid containing 0.1% of H14 is given topically to the eye of a person suffering from elevated intraocular pressure. A few hours after administration, the person's intraocular pressure is reduced. The drop is administered twice a day, and pressure remains low for as long as the treatment is continued.

Treatment Example 15

An aqueous liquid containing 0.1% of H15 is given topically to the eye of a person suffering from elevated intraocular pressure. A few hours after administration, the person's intraocular pressure is reduced. The drop is administered twice a day, and pressure remains low for as long as the treatment is continued.

Treatment Example 16

An aqueous liquid containing 0.1% of H16 is given topically to the eye of a person suffering from elevated intraocular pressure. A few hours after administration, the person's intraocular pressure is reduced. The drop is administered twice a day, and pressure remains low for as long as the treatment is continued.

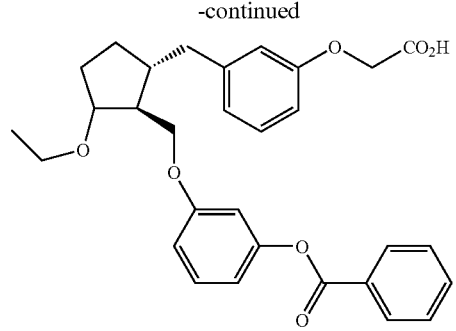

H12

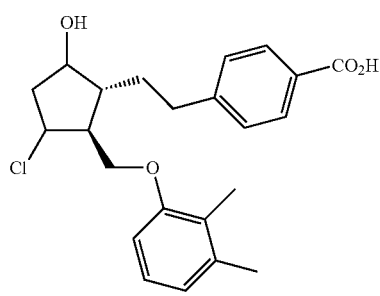

H13

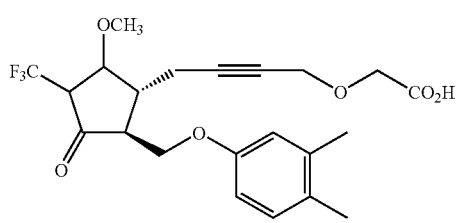

H14

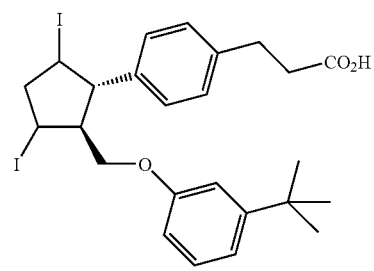

H9

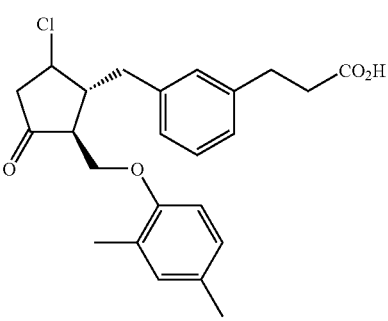

H15

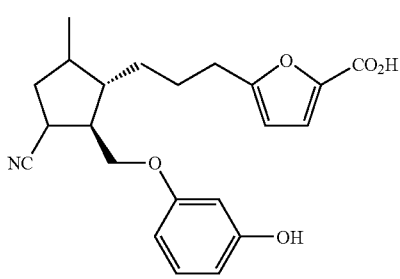

H10

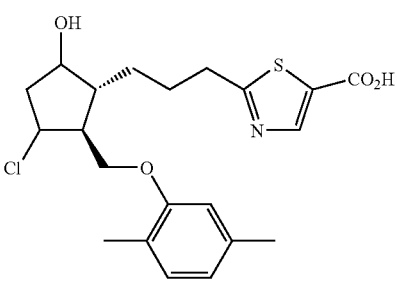

H16

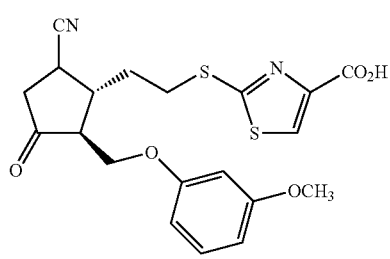

H11

Treatment Example 17

An aqueous liquid containing 0.1% of H17 is given topically to the eye of a person suffering from elevated intraocular pressure. A few hours after administration, the person's intraocular pressure is reduced. The drop is administered twice a day, and pressure remains low for as long as the treatment is continued.

Treatment Example 18

An aqueous liquid containing 0.1% of H18 is given topically to the eye of a person suffering from elevated intraocular pressure. A few hours after administration, the person's intraocular pressure is reduced. The drop is administered twice a day, and pressure remains low for as long as the treatment is continued.

Treatment Example 19

An aqueous liquid containing 0.1% of H19 is given topically to the eye of a person suffering from elevated intraocular pressure. A few hours after administration, the person's intraocular pressure is reduced. The drop is administered twice a day, and pressure remains low for as long as the treatment is continued.

Treatment Example 20

An aqueous liquid containing 0.1% of $H_2O$ is given topically to the eye of a person suffering from elevated intraocular pressure. A few hours after administration, the person's intraocular pressure is reduced. The drop is administered twice a day, and pressure remains low for as long as the treatment is continued.

Treatment Example 21

An aqueous liquid containing 0.1% of H21 is given topically to the eye of a person suffering from elevated intraocular pressure. A few hours after administration, the person's intraocular pressure is reduced. The drop is administered twice a day, and pressure remains low for as long as the treatment is continued.

Treatment Example 22

An aqueous liquid containing 0.1% of H22 is given topically to the eye of a person suffering from elevated intraocular pressure. A few hours after administration, the person's intraocular pressure is reduced. The drop is administered twice a day, and pressure remains low for as long as the treatment is continued.

Treatment Example 23

An aqueous liquid containing 0.1% of H23 is given topically to the eye of a person suffering from elevated intraocular pressure. A few hours after administration, the person's intraocular pressure is reduced. The drop is administered twice a day, and pressure remains low for as long as the treatment is continued.

Treatment Example 24

An aqueous liquid containing 0.1% of H24 is given topically to the eye of a person suffering from elevated intraocular pressure. A few hours after administration, the person's intraocular pressure is reduced. The drop is administered twice a day, and pressure remains low for as long as the treatment is continued.

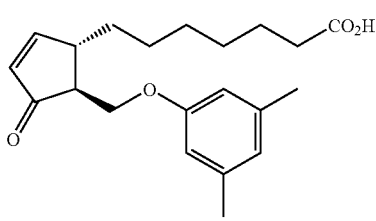

H17

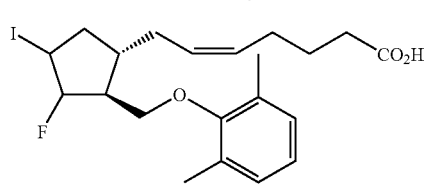

H18

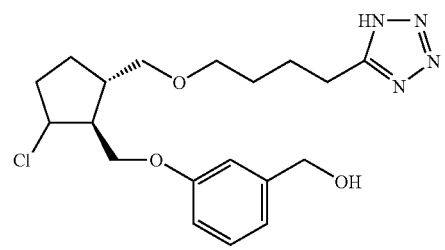

H19

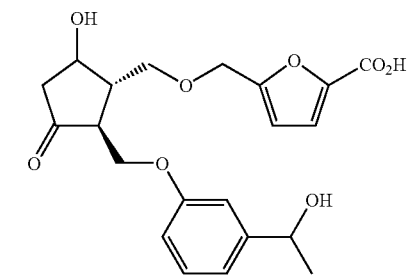

H20

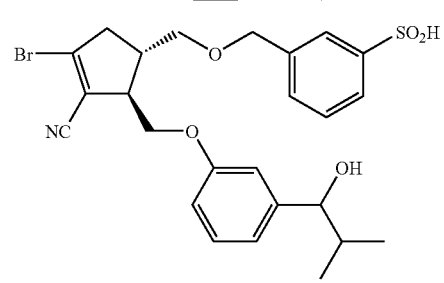

H21

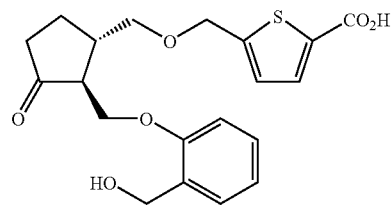

H22

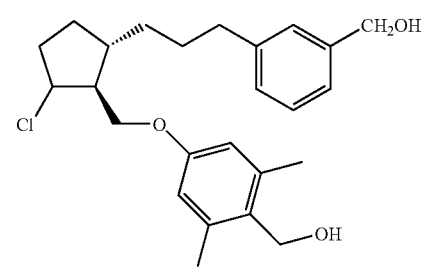

H23

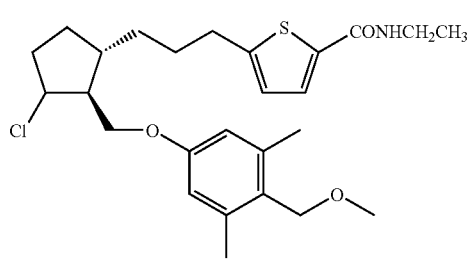

H24

Treatment Example 25

An aqueous liquid containing 0.1% of H25 is given topically to the eye of a person suffering from elevated intraocular pressure. A few hours after administration, the person's intraocular pressure is reduced. The drop is administered twice a day, and pressure remains low for as long as the treatment is continued.

Treatment Example 26

An aqueous liquid containing 0.1% of H26 is given topically to the eye of a person suffering from elevated intraocular pressure. A few hours after administration, the person's intraocular pressure is reduced. The drop is administered twice a day, and pressure remains low for as long as the treatment is continued.

Treatment Example 27

An aqueous liquid containing 0.1% of H27 is given topically to the eye of a person suffering from elevated intraocular pressure. A few hours after administration, the person's intraocular pressure is reduced. The drop is administered twice a day, and pressure remains low for as long as the treatment is continued.

Treatment Example 28

An aqueous liquid containing 0.1% of H28 is given topically to the eye of a person suffering from elevated intraocular pressure. A few hours after administration, the person's intraocular pressure is reduced. The drop is administered twice a day, and pressure remains low for as long as the treatment is continued.

Treatment Example 29

An aqueous liquid containing 0.1% of H29 is given topically to the eye of a person suffering from elevated intraocular pressure. A few hours after administration, the person's intraocular pressure is reduced. The drop is administered twice a day, and pressure remains low for as long as the treatment is continued.

Treatment Example 30

An aqueous liquid containing 0.1% of H30 is given topically to the eye of a person suffering from elevated intraocular pressure. A few hours after administration, the person's intraocular pressure is reduced. The drop is administered twice a day, and pressure remains low for as long as the treatment is continued.

Treatment Example 31

An aqueous liquid containing 0.1% of H31 is given topically to the eye of a person suffering from elevated intraocular pressure. A few hours after administration, the person's intraocular pressure is reduced. The drop is administered twice a day, and pressure remains low for as long as the treatment is continued.

Treatment Example 32

An aqueous liquid containing 0.1% of H32 is given topically to the eye of a person suffering from elevated intraocular pressure. A few hours after administration, the person's intraocular pressure is reduced. The drop is administered twice a day, and pressure remains low for as long as the treatment is continued.

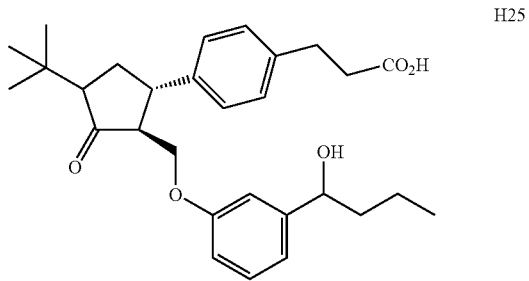

H25

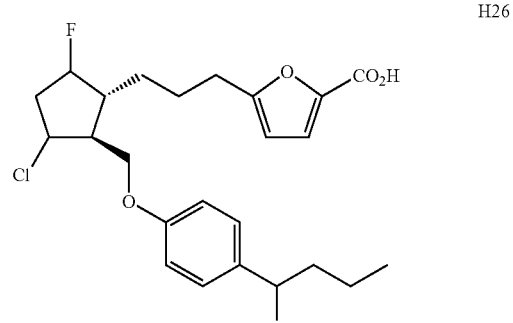

H26

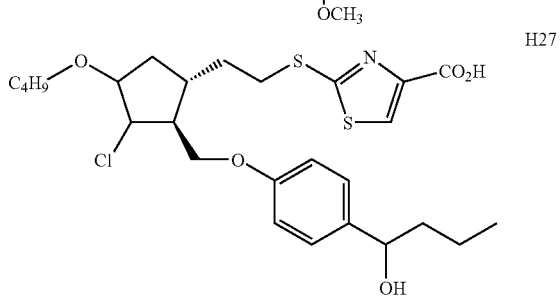

H27

-continued

H28
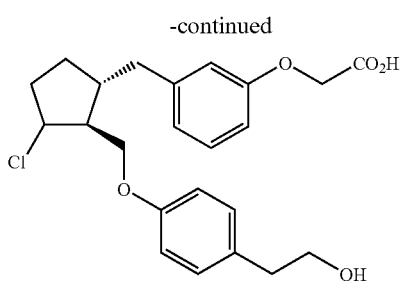

H29
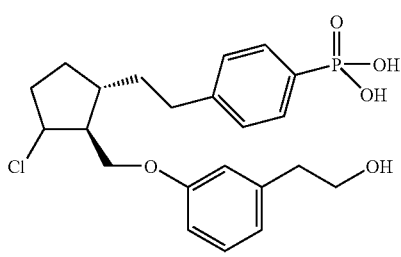

H30
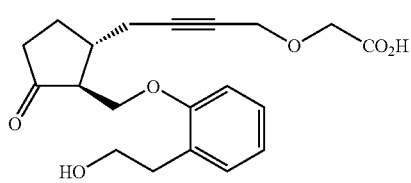

H31
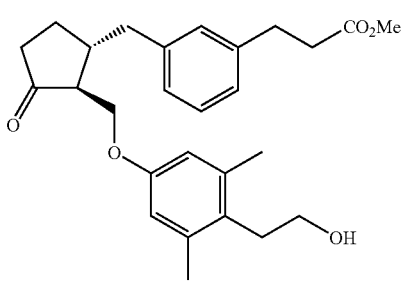

H32
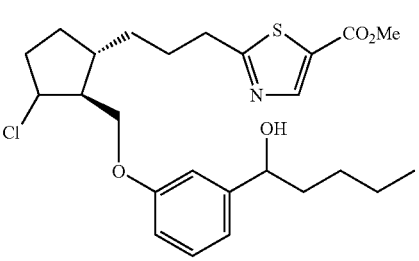

Treatment Example 33

An aqueous liquid containing 0.1% of H33 is given topically to the eye of a person suffering from elevated intraocular pressure. A few hours after administration, the person's intraocular pressure is reduced. The drop is administered twice a day, and pressure remains low for as long as the treatment is continued.

Treatment Example 34

An aqueous liquid containing 0.1% of H34 is given topically to the eye of a person suffering from elevated intraocular pressure. A few hours after administration, the person's intraocular pressure is reduced. The drop is administered twice a day, and pressure remains low for as long as the treatment is continued.

Treatment Example 35

An aqueous liquid containing 0.1% of H35 is given topically to the eye of a person suffering from elevated intraocular pressure. A few hours after administration, the person's intraocular pressure is reduced. The drop is administered twice a day, and pressure remains low for as long as the treatment is continued.

Treatment Example 36

An aqueous liquid containing 0.1% of H36 is given topically to the eye of a person suffering from elevated intraocular pressure. A few hours after administration, the person's intraocular pressure is reduced. The drop is administered twice a day, and pressure remains low for as long as the treatment is continued.

Treatment Example 37

An aqueous liquid containing 0.1% of H37 is given topically to the eye of a person suffering from elevated intraocular pressure. A few hours after administration, the person's intraocular pressure is reduced. The drop is administered twice a day, and pressure remains low for as long as the treatment is continued.

Treatment Example 38

An aqueous liquid containing 0.1% of H38 is given topically to the eye of a person suffering from elevated intraocular pressure. A few hours after administration, the person's intraocular pressure is reduced. The drop is administered twice a day, and pressure remains low for as long as the treatment is continued.

Treatment Example 39

An aqueous liquid containing 0.1% of H39 is given topically to the eye of a person suffering from elevated intraocular pressure. A few hours after administration, the person's intraocular pressure is reduced. The drop is administered twice a day, and pressure remains low for as long as the treatment is continued.

Treatment Example 40

An aqueous liquid containing 0.1% of H40 is given topically to the eye of a person suffering from elevated intraocular pressure. A few hours after administration, the person's intraocular pressure is reduced. The drop is administered twice a day, and pressure remains low for as long as the treatment is continued.

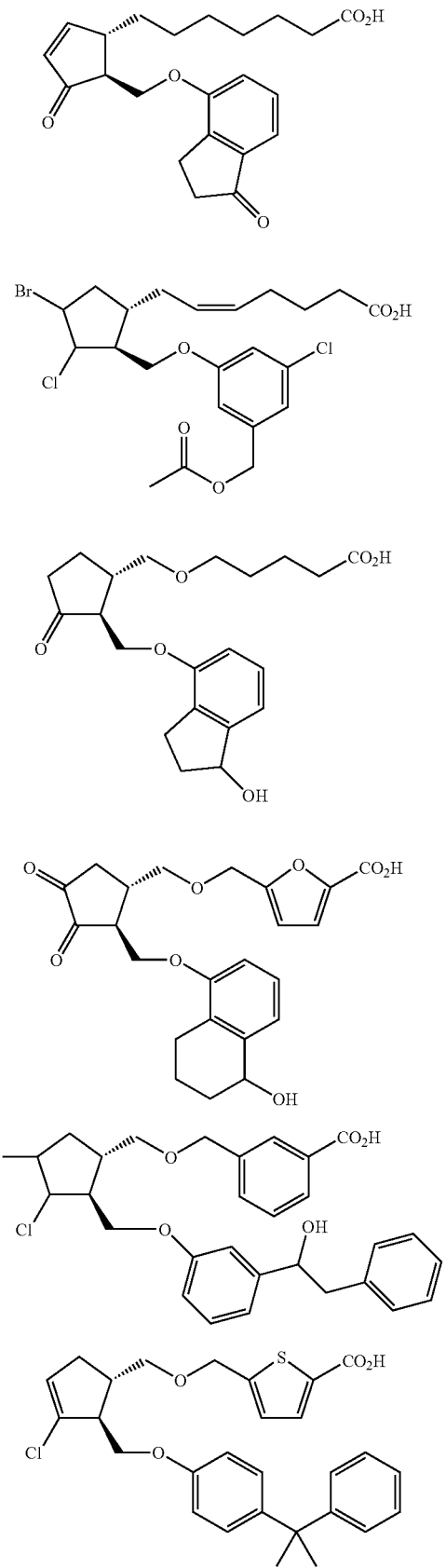
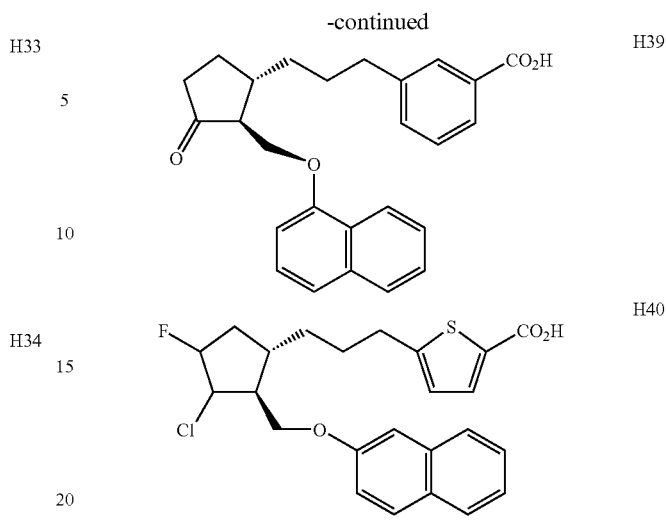

Treatment Example 41

An aqueous liquid containing 0.1% of H41 is given topically to the eye of a person suffering from elevated intraocular pressure. A few hours after administration, the person's intraocular pressure is reduced. The drop is administered twice a day, and pressure remains low for as long as the treatment is continued.

Treatment Example 42

An aqueous liquid containing 0.1% of H42 is given topically to the eye of a person suffering from elevated intraocular pressure. A few hours after administration, the person's intraocular pressure is reduced. The drop is administered twice a day, and pressure remains low for as long as the treatment is continued.

Treatment Example 43

An aqueous liquid containing 0.1% of H43 is given topically to the eye of a person suffering from elevated intraocular pressure. A few hours after administration, the person's intraocular pressure is reduced. The drop is administered twice a day, and pressure remains low for as long as the treatment is continued.

Treatment Example 44

An aqueous liquid containing 0.1% of H44 is given topically to the eye of a person suffering from elevated intraocular pressure. A few hours after administration, the person's intraocular pressure is reduced. The drop is administered twice a day, and pressure remains low for as long as the treatment is continued.

Treatment Example 45

An aqueous liquid containing 0.1% of H45 is given topically to the eye of a person suffering from elevated intraocular pressure. A few hours after administration, the person's intraocular pressure is reduced. The drop is administered twice a day, and pressure remains low for as long as the treatment is continued.

Treatment Example 46

An aqueous liquid containing 0.1% of H46 is given topically to the eye of a person suffering from elevated intraocular pressure. A few hours after administration, the person's intraocular pressure is reduced. The drop is administered twice a day, and pressure remains low for as long as the treatment is continued.

Treatment Example 47

An aqueous liquid containing 0.1% of H47 is given topically to the eye of a person suffering from elevated intraocular pressure. A few hours after administration, the person's intraocular pressure is reduced. The drop is administered twice a day, and pressure remains low for as long as the treatment is continued.

Treatment Example 48

An aqueous liquid containing 0.1% of H48 is given topically to the eye of a person suffering from elevated intraocular pressure. A few hours after administration, the person's intraocular pressure is reduced. The drop is administered twice a day, and pressure remains low for as long as the treatment is continued.

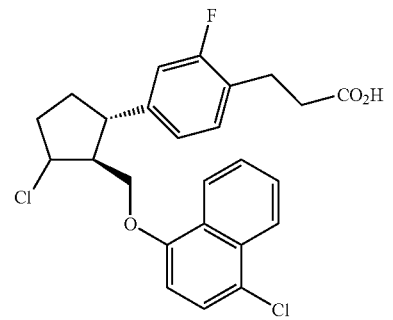

H41

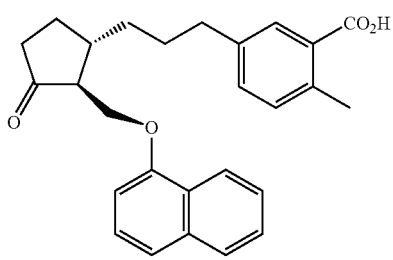

H42

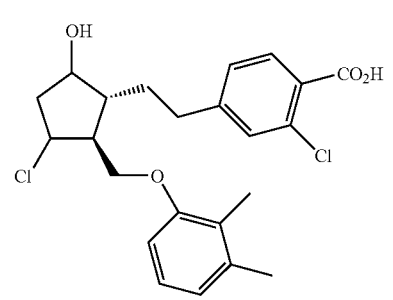

H43

-continued

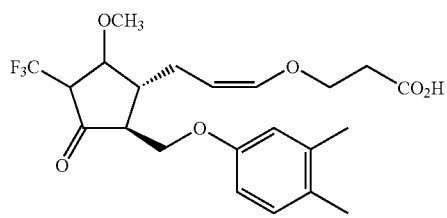

H44

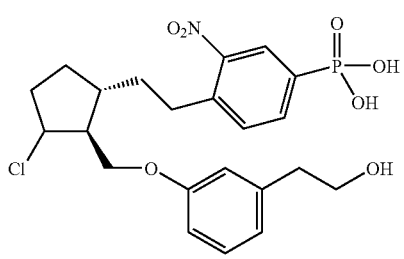

H45

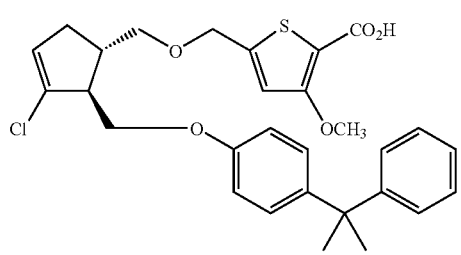

H46

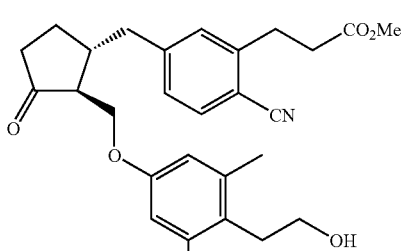

H47

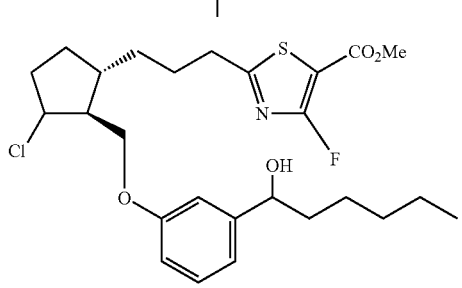

H48

Treatment Example 49

An aqueous liquid containing 0.1% of H49 is given topically to the eye of a person suffering from elevated intraocular pressure. A few hours after administration, the person's intraocular pressure is reduced. The drop is administered twice a day, and pressure remains low for as long as the treatment is continued.

Treatment Example 50

An aqueous liquid containing 0.1% of H50 is given topically to the eye of a person suffering from elevated intraocular pressure. A few hours after administration, the person's intraocular pressure is reduced. The drop is administered twice a day, and pressure remains low for as long as the treatment is continued.

Treatment Example 51

An aqueous liquid containing 0.1% of H51 is given topically to the eye of a person suffering from elevated intraocular pressure. A few hours after administration, the person's intraocular pressure is reduced. The drop is administered twice a day, and pressure remains low for as long as the treatment is continued.

Treatment Example 52

An aqueous liquid containing 0.1% of H52 is given topically to the eye of a person suffering from elevated intraocular pressure. A few hours after administration, the person's intraocular pressure is reduced. The drop is administered twice a day, and pressure remains low for as long as the treatment is continued.

Treatment Example 53

An aqueous liquid containing 0.1% of H53 is given topically to the eye of a person suffering from elevated intraocular pressure. A few hours after administration, the person's intraocular pressure is reduced. The drop is administered twice a day, and pressure remains low for as long as the treatment is continued.

Treatment Example 54

An aqueous liquid containing 0.1% of H54 is given topically to the eye of a person suffering from elevated intraocular pressure. A few hours after administration, the person's intraocular pressure is reduced. The drop is administered twice a day, and pressure remains low for as long as the treatment is continued.

Treatment Example 55

An aqueous liquid containing 0.1% of H55 is given topically to the eye of a person suffering from elevated intraocular pressure. A few hours after administration, the person's intraocular pressure is reduced. The drop is administered twice a day, and pressure remains low for as long as the treatment is continued.

Treatment Example 56

An aqueous liquid containing 0.1% of H56 is given topically to the eye of a person suffering from elevated intraocular pressure. A few hours after administration, the person's intraocular pressure is reduced. The drop is administered twice a day, and pressure remains low for as long as the treatment is continued.

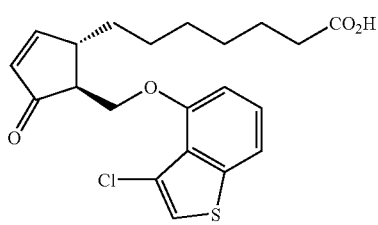

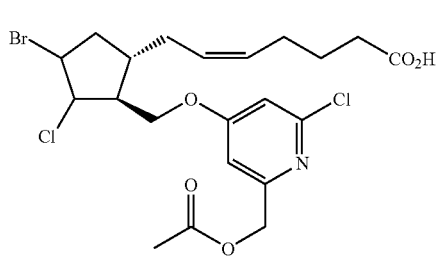

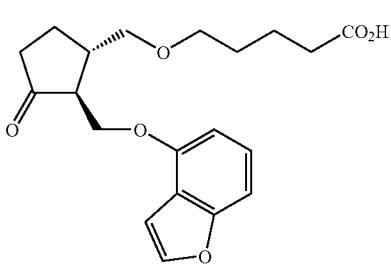

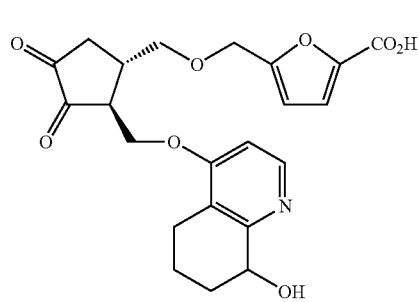

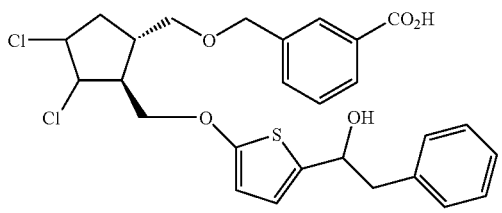

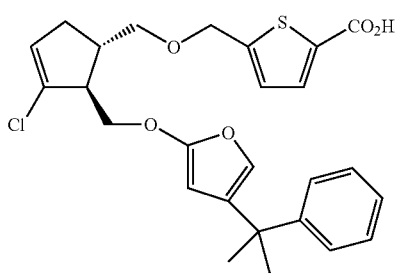

-continued

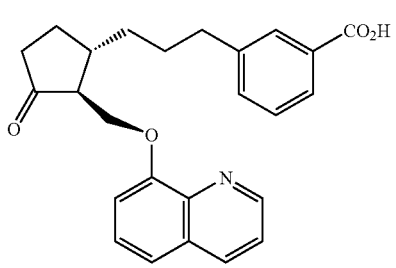
H55

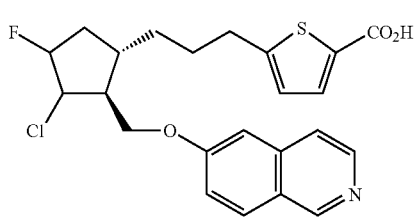
H56

Treatment Example 57

An aqueous liquid containing 0.1% of H57 is given topically to the eye of a person suffering from elevated intraocular pressure. A few hours after administration, the person's intraocular pressure is reduced. The drop is administered twice a day, and pressure remains low for as long as the treatment is continued.

Treatment Example 58

An aqueous liquid containing 0.1% of H58 is given topically to the eye of a person suffering from elevated intraocular pressure. A few hours after administration, the person's intraocular pressure is reduced. The drop is administered twice a day, and pressure remains low for as long as the treatment is continued.

Treatment Example 59

An aqueous liquid containing 0.1% of H59 is given topically to the eye of a person suffering from elevated intraocular pressure. A few hours after administration, the person's intraocular pressure is reduced. The drop is administered twice a day, and pressure remains low for as long as the treatment is continued.

Treatment Example 60

An aqueous liquid containing 0.1% of H60 is given topically to the eye of a person suffering from elevated intraocular pressure. A few hours after administration, the person's intraocular pressure is reduced. The drop is administered twice a day, and pressure remains low for as long as the treatment is continued.

Treatment Example 61

An aqueous liquid containing 0.1% of H61 is given topically to the eye of a person suffering from elevated intraocular pressure. A few hours after administration, the person's intraocular pressure is reduced. The drop is administered twice a day, and pressure remains low for as long as the treatment is continued.

Treatment Example 62

An aqueous liquid containing 0.1% of H62 is given topically to the eye of a person suffering from elevated intraocular pressure. A few hours after administration, the person's intraocular pressure is reduced. The drop is administered twice a day, and pressure remains low for as long as the treatment is continued.

Treatment Example 63

An aqueous liquid containing 0.1% of H63 is given topically to the eye of a person suffering from elevated intraocular pressure. A few hours after administration, the person's intraocular pressure is reduced. The drop is administered twice a day, and pressure remains low for as long as the treatment is continued.

Treatment Example 64

An aqueous liquid containing 0.1% of H64 is given topically to the eye of a person suffering from elevated intraocular pressure. A few hours after administration, the person's intraocular pressure is reduced. The drop is administered twice a day, and pressure remains low for as long as the treatment is continued.

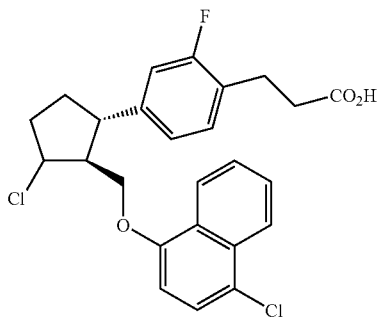
H57

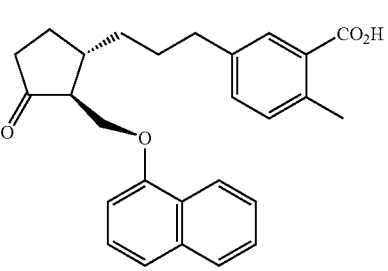
H58

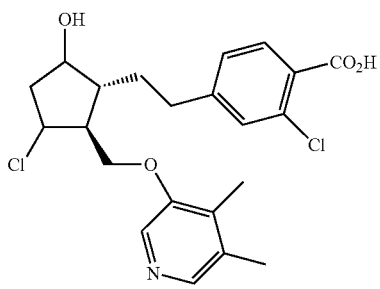
H59

-continued

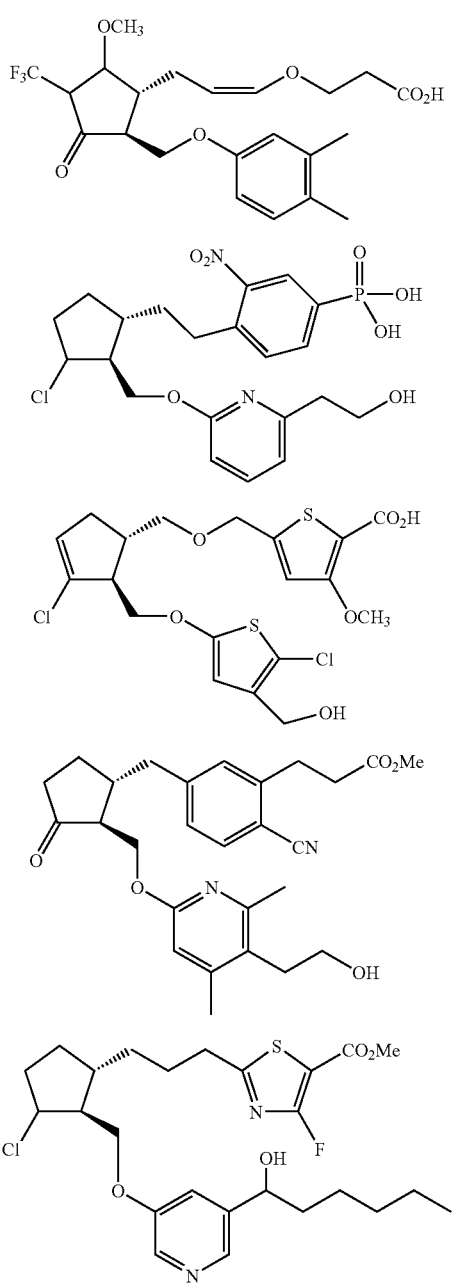

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:
1. A compound having a formula selected from:

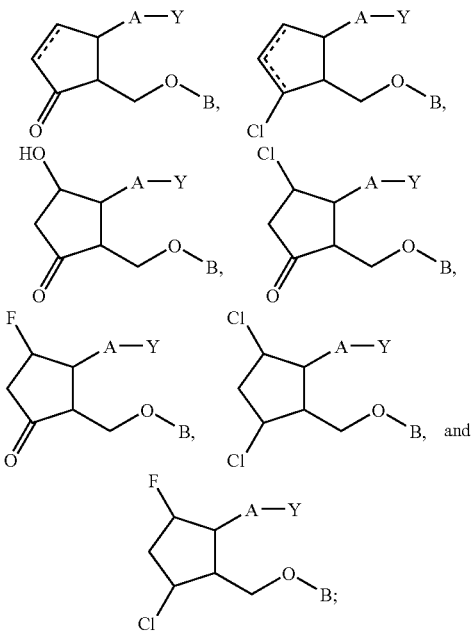

or a pharmaceutically acceptable salt thereof, or a prodrug thereof;
wherein a dashed line represents the presence or absence of a bond;
Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, and $SO_2NHR^2$;
wherein $R^2$ is independently H, $C_1$-$C_6$ alkyl, unsubstituted phenyl, or unsubstituted biphenyl;
A is —$(CH_2)_6$—, cis —$CH_2CH=CH$—$(CH_2)3$-, or —$CH_2C\equiv C$—$(CH_2)3$-, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;
B is aryl or heteroaryl.
2. A compound having a formula

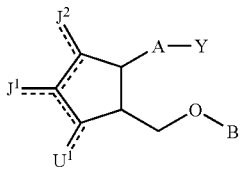

or a pharmaceutically acceptable salt thereof, or a prodrug thereof;
wherein a dashed line represents the presence or absence of a bond;
Y is selected from $CO_2R^2$, $CON(R^2)_2$, $CON(OR^2)R^2$, $CON(CH_2CH_2OH)_2$, $CONH(CH_2CH_2OH)$, $P(O)(OH)_2$, $CONHSO_2R^2$, $SO_2N(R^2)_2$, and $SO_2NHR^2$, wherein $R^2$ is independently H, $C_1$-$C_6$ alkyl, unsubstituted phenyl, or unsubstituted biphenyl;
A is —$(CH_2)_3Ar$—, —$O(CH_2)_2Ar$—, —$CH_2OCH_2Ar$—, —$(CH_2)_2OAr$, —$O(CH_2)_2Ar$—, —$CH_2OCH_2Ar$—, or —(CH$_2$)$_2$OAr, wherein Ar is interthienylene, interthiazolylene, or interoxazolylene;

U$^1$ is independently O; S; F; Cl; Br; I; CN; or O-alkyl having 1, 2, 3, 4, 5 or 6 carbon atoms;

J$^1$ and J$^2$ are independently hydrogen; F; Cl, Br; I; O; OH; CN; O-alkyl having 1, 2, 3, 4, 5 or 6 carbon atoms; alkyl having 1, 2, 3, 4, 5, or 6 carbon atoms; or CF$_3$; and B is aryl or heteroaryl.

3. The compound of claim 2 wherein Ar is interthienylene.

4. The compound of claim 2 wherein Ar is interthiazolylene.

5. The compound of claim 2 wherein Ar is interoxazolylene.

6. The compound of claim 3 wherein A is 5-(3-propyl)thiophen-2-yl.

7. The compound of claim 1 having the formula or a pharmaceutically acceptable salt thereof or a prodrug thereof.

8. The compound of claim 1 having the formula or a pharmaceutically acceptable salt thereof or a prodrug thereof.

9. The compound of claim 1 having the formula or a pharmaceutically acceptable salt thereof or a prodrug thereof.

10. The compound of claim 1 having the formula or a pharmaceutically acceptable salt thereof or a prodrug thereof.

11. The compound of claim 1 having the formula or a pharmaceutically acceptable salt thereof or a prodrug thereof.

12. The compound of claim 1 having the formula or a pharmaceutically acceptable salt thereof or a prodrug thereof.

13. The compound of claim 1 having the formula or a pharmaceutically acceptable salt thereof or a prodrug thereof.

14. The compound of claim 1 wherein A is selected from:

15. The compound of claim 1 wherein A is selected from:
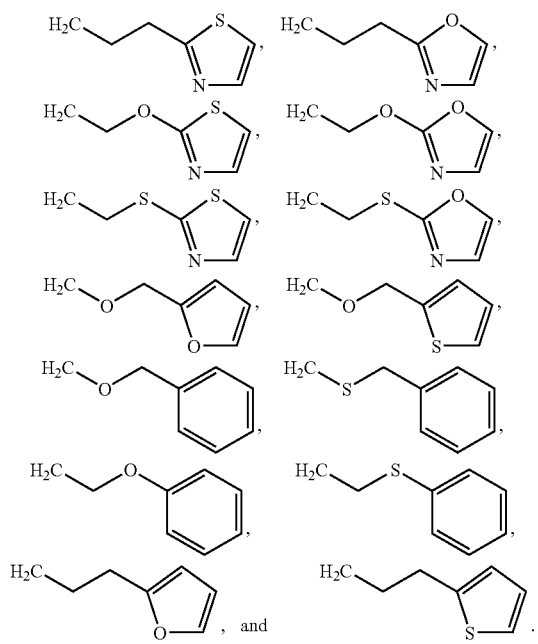
16. The compound of claim 6 wherein B is substituted phenyl.
17. The compound of claim 16 further represented by the formula:
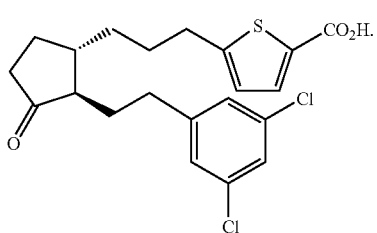
18. The compound of claim 16 further represented by the formula:
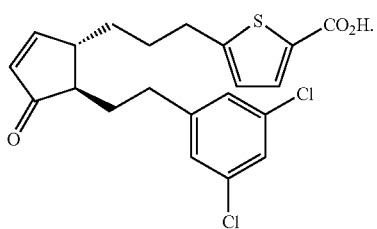
* * * * *